US008101400B2

(12) United States Patent
Rolston et al.

(10) Patent No.: US 8,101,400 B2
(45) Date of Patent: Jan. 24, 2012

(54) GRASS BASED AVIAN DETERRENT

(75) Inventors: Maurice Philip Rolston, Christchurch RD2 (NZ); Christopher Gerald Lee Pennell, Canterbury (NZ)

(73) Assignee: Grasslanz Technology Limited, Palmerston North (NZ)

( * ) Notice: Subject to any disclaimer, the term of this patent is extended or adjusted under 35 U.S.C. 154(b) by 463 days.

(21) Appl. No.: 12/110,159

(22) Filed: Apr. 25, 2008

(65) Prior Publication Data

US 2008/0299144 A1 Dec. 4, 2008

Related U.S. Application Data

(60) Provisional application No. 60/914,656, filed on Apr. 27, 2007.

(51) Int. Cl.
*C12N 1/14* (2006.01)
(52) U.S. Cl. .................................... 435/256.4
(58) Field of Classification Search ......................... None
See application file for complete search history.

(56) References Cited

U.S. PATENT DOCUMENTS

| 6,072,107 | A | 6/2000 | Latch et al. | |
|---|---|---|---|---|
| 6,111,170 | A | 8/2000 | Latch et al. | |
| 7,642,424 | B2 * | 1/2010 | Van Hanja et al. | 800/320 |

FOREIGN PATENT DOCUMENTS

| WO | WO97/037540 | 10/1997 |
|---|---|---|
| WO | WO00/065912 | 11/2000 |
| WO | WO01/078510 | 10/2001 |

OTHER PUBLICATIONS

Siegel et al., J. Chem. Ecol., 1990, vol. 16, pp. 3301-3315.*
Leuchtmann et al 2000, Journal of chemical Ecology vol. 26, No. 4. pp. 1025-1036.*
Blackwell, et al., "Efficacy of aircraft landing lights in stimulating avoidance behavior in birds", *J. of Wildlife Management*, (Jul. 2004) 68(3): 725-732.
Clay, Keith, "Symbiosis and the Regulation of Communities" *Amer. Zool.*, (2001) 41: 810-824.
Conover, et al., "Feeding Preferences and Changes in Mass of Canada Geese Grazing Endophyte-Infected Tall Fescue" *The Condor*, (1996) 98: 859-862.
Dolbeer, et al., "Anthraquinone Formulation (Flight Control) Shows Promise as Avian Feeding Repellent" *J. of Wildlife Management*, (1998) 62(4): 1558-1564.
Dolbeer, et al., "Ranking the hazard level of wildlife species to aviation", *Wildlife Society Bulletin*, (2000) 28(2): 372-378.
Durham, et al., "Effect of endophyte consumption on food intake, growth and reproduction in prairie voles", *Canadian J. of Zoology*, (May 1998) 76: 960-969.
Gosser, et al., *Managing Problems Caused by Urban Canada Geese*, Berryman Institute Publication 13, (1997) Utah State University, Logan.
Madej, et al., "Avian seed preference and weight loss experiments: the effect of fungal endophyte-infected tall fescue seeds" *Oecologia*, (1991) 88: 296-302.
Christensen, et al., "Occurrence of the fungal endophyte *Neotyphodium coenophialum* in leaf blades of tall fescue and impOlications for stock health" *NZ J of Ag Res* (1998) 41: 595-602.

* cited by examiner

*Primary Examiner* — David H Kruse
(74) *Attorney, Agent, or Firm* — Knobbe, Martens Olson & Bear LLP

(57) ABSTRACT

The invention relates to uses and methods relating to grass and endophyte combinations to repel avian species from the grass and endophyte combination. In particular, methods are described to select grass and endophyte combinations in order to enhance or maximise the repellent effect. Preferred endophyte and grass combinations are described which are based on the selection methods and include AR4, AR5, AR8 and AR94 (Deposit Nos. V07/029054, V07/029055, V071029056, V07/029057) in *Lolium* cultivars as well as AR601, AR602, AR603, and AR604 (Deposit Nos. V07/029058, V07/029059, V07/029060, V07/029061) in *Festuca* cultivars.

24 Claims, 12 Drawing Sheets

GRASS BASED AVIAN DETERRENT

CROSS-REFERENCE TO RELATED APPLICATIONS

This application claims priority to U.S. Provisional Application No. 60/914,656, filed on Apr. 27, 2007, the entire disclosure of which is incorporated herein by reference.

BACKGROUND OF THE INVENTION

1. Field of the Invention

This invention relates to a grass based avian deterrent. More specifically, the invention relates to a grass cultivar and endophyte combination that produces alkaloid toxins sufficient to deter avian species from the grass cultivar and endophyte combination.

2. Description of the Related Art

Avian populations can be undesirable in certain environments. Bird populations can have a devastating effect on horticultural and agricultural crops, cause severe damage to an aircraft in the event of a bird strike and can simply be an irritant, for example in recreational areas.

More specifically, bird populations can quickly destroy fruit crop(s) such as apricots, peaches, apples, kiwifruit and the like through feeding on the ripening fruit. Similarly, birds can also significantly reduce the harvest of seed or grains from various cereal and grain crops (e.g., wheat production).

For the aviation industry, the problem is highly significant as a bird strike incident can severely disrupt normal aircraft handling and can even be a significant causal factor in aircraft crashes.

In the above situations as well as in general, bird populations around water ways or in recreation areas and even around domestic housing can also be a nuisance. Other problems such as water and ground contamination from bird excrement can also be significant.

Various attempts have been made to deter birds from an area. These act on primary initial response mechanisms e.g., a loud noise or act using a secondary response, for example, making the bird ill by feeding the bird bait which includes a chemical irritant.

In more detail, primary deterrents include acoustical distress calls, gas guns, lights, lasers, dogs, falconry, kites and balloons which all work to frighten the birds from an area. Other methods such as sticky pastes, spikes, wires and netting may also be used.

Secondary deterrents include a (UV) light product known as ultra violet anthraquinone, methyl anthranilate (MA), taste aversion sprays and poisons such as methiocarb carbamate (Mesurol 50 HBT).

However, each of the above methods has disadvantages. Primary deterrents generally do not work over a longer term as birds 'learn' that the danger is not real. In addition, these methods usually involve significant financial and labour costs to install and run the devices and arrangements used to deter the birds.

Secondary methods have the obvious problem of allowing at least a first strike by the birds. In the case of baits, the birds may not all eat the bait and hence it may take some time before the full deterrent effect is obtained. In addition the deterrents need to be re-applied on a regular basis and in some environments, simply cannot be used for risk of the chemical agents contaminating food or water.

A further problem is that the above methods need to be carried out numerous times during a given period of time. For example, baits may need to be used on numerous occasions to achieve the deterrent effect and, later another cycle may need to be completed to deal with new populations of birds arriving.

Therefore, the subject matter of the present invention is drawn to providing the public with useful compositions and their uses as well as methods for addressing such problems.

SUMMARY OF THE INVENTION

For the purposes of this specification, the term 'endophyte' or grammatical variations thereof refer to fungi living within cultivated grasses or axenic culture medium.

The term 'cultivated grasses' or 'cultivar' or grammatical variations thereof refer to varieties of grasses that have been created or selected intentionally and maintained through cultivation.

The grass cultivar may also be a synthetic grass cultivar. The term 'synthetic grass cultivar' refers to the grass cultivar being produced through selective breeding techniques including selection and development from an uncultivated population. For example, a synthetic grass cultivar refers to where—
   (a) reproducable units are from a cross-pollinated crop which can encompass clones or inbred grasses;
   (b) materials used are selected from their performance in combining ability or progeny tests;
   (c) the cultivar is constituted by random inter-mating of the units;
   (d) the units are maintained so that the synthetic can be reconstituted.

The term 'herbage' refers to the plant generally including the stems, pseudostems, leaves, flowers and seeds.

The term 'combination' or grammatical variations thereof refer to the combination of an endophyte and a grass cultivar infected with endophyte fungi.

The term 'pests' for the purpose of this invention refers to insects, birds or other animals that destroy or harm plants, crops, food, or even endanger or threaten human safety.

The term 'low temperature' for the purpose of this invention include temperatures up to and including 7° C. While the term 'high temperature' for the purpose of this invention, include temperatures from 27° C. and above.

The term 'sufficient levels' used in the context of alkaloid compounds in the grass refers to the levels being sufficient to exhibit a deterrent effect on pests as defined above.

The term 'AR601, AR602, AR603, AR604, AR4, AR5, AR8 or AR94 endophyte' refers to an endophyte which can be distinguished from other endophytes through their particular microsatellite pattern. In particular, Example 13 below summarizes these endophytes and the simple sequence repeat sizes at various alleles. Also described is the methodology for achieving the microsatellite pattern. The endophyte strains have also been deposited at NMI (Australian Institute) on 23 Jul. 2007 and accorded with accession numbers: V07/029058, V07/029059, V07/029060, V07/029061, V07029054, V07/029055, V07/029056, V07/029057, respectively.

Embodiments of the present invention provide the use of an endophyte and grass cultivar combination to repel avian species from the grass combination. The grass combination is characterised as a combination that includes a level of at least one ergot-peptide alkaloid sufficient to deter the avian species from the grass combination.

The inventors have found that by manipulating the properties of grass and endophyte combinations, endophyte and grass combinations can be produced and selected to repel avian species from the grass. This has significant advantages as the grass is a relatively permanent fixture and easy to maintain once it is sown. Therefore the deterrent can be used for minimal cost and labour.

According to one an aspect of the present invention, there is provided an endophyte and grass cultivar combination that repels avian species from the combination, characterised in that the endophyte in the combination produces ergovaline alkaloid compound sufficient to repel the avian species from the cultivar herbage and seeds produced therefrom.

According to a further aspect of the present invention, there is provided an endophyte and grass cultivar combination including an endophyte selected from the group consisting of: AR601, AR602, AR603, AR604, AR4, AR5, AR8 and AR94 (Deposit Nos. V07/029058, V07/029059, V07/029060, V07/029061, V07/029054, V07/029055, V07/029056 V07/029057, and combinations thereof;

characterised in that avian species are repelled from the cultivar herbage and seeds produced therefrom.

Preferably, the endophyte may be from the genera *Neotyphodium*. More preferably, the endophyte may be from the *Neotyphodium coenophialum* species. More preferably, the endophyte may be selected from the group consisting of: AR601, AR602, AR603, AR604, AR4, AR5, AR8, AR94 (Deposit Nos. V07/029058, V07/029059, V07/029060, V07/029061, V07029054, V07/029055, V07/029056, V07/029057, and combinations thereof. It is appreciated that other endophytes may be used without departing from the scope of the invention as herein described. For example, as noted above, a characteristic in determining repellent effect is the amount of ergovaline alkaloid. Other endophytes can be found that also produce levels of ergovaline alkaloid compounds sufficient to result in a repellent effect.

Preferably, the ergovaline alkaloid compound or compounds are present in at least a portion of the cultivar herbage. In one embodiment, the ergovaline alkaloid is present in at least the pseudostem and/or seeds of the cultivar. Preferably, the combinations as described above include repellent levels of ergovaline throughout the herbage of the plant including the pseudostem as well as the leaf, stems and seeds. Levels are provided with respect to the pseudostem to illustrate alkaloid spread through the herbage. It should be apparent to one of skill in the art that the ergovaline alkaloid (and other alkaloids) can be present in other parts of the grass cultivar herbage and that reference to the pseudostem should not be seen as being limiting.

Although reference is made in this specification with respect to ergovaline, it should be appreciated by those skilled in the art that embodiments of the invention may be applied to other ergot-peptide alkaloid compounds.

According to a further aspect of the present invention, there is provided an endophyte and a *Festuca* grass cultivar combination, or grass cultivars exemplified by *Festuca* characteristics, that repels avian species from the combination, characterised in that the endophyte in the combination produces a level of at least 3 ppm of ergovaline alkaloid compound within a portion of the cultivar herbage and seeds produced therefrom.

Preferably, the *Festuca* grass cultivar may be tall fescue (*Festuca arundinacea*, or its synonyms) meadow fescue (*F. pratensis*), chewing fescue (*F. rubra*), and the like or other *Festuca* grass cultivars with similar characteristics, or other grass species such as brown tops (*Agrostis tenuis*) and other *Agrostis* species.

Preferred endophytes for Festuca grass cultivar are endophytes selected from the group consisting of: AR601, AR602, AR603, AR604, (Deposit Nos. V07/029058, V07/029059, V07/029060, V07/029061) and combinations thereof. However, it should be appreciated that other endophytes may be used together with other grass species which produce similar levels of ergovaline without departing from the scope of the invention.

According to a further aspect of the present invention, there is provided an endophyte and a *Lolium* grass cultivar combination, or grass cultivars exemplified by *Lolium* characteristics, that repels avian species from the combination, characterised in that the endophyte in the combination produces a level of at least 3 ppm of ergovaline alkaloid compound within a portion of the cultivar herbage and seeds produced therefrom.

In preferred embodiments, the grass may be perennial ryegrass or *Lolium perenne*. In some other embodiments other *Lolium* cultivars may be used including *L. multiflorum*, *L. hybridum* and hybrids thereof.

Preferred endophytes for Lolium grass cultivars are endophytes selected from the group consisting of: of AR4, AR5, AR8, AR94 (Deposit Nos. V07/029054, V07/029055, V07/029056, V07/029057 and combinations thereof. However, it should be appreciated that other endophytes and *Lolium* cultivars may be used which produce similar levels of ergovaline without departing from the scope of the invention.

Preferably, the grass and endophyte combination repel avian species via a secondary deterrent effect. More preferably, the repellent effect is a secondary effect resulting from a post digestive feedback (PDF) mechanism.

In preferred embodiments, the avian species are birds including waterfowl such as geese, seabirds such as seagulls and city birds (*Passeriformes* bird types) such as sparrows, and finches. In further embodiments, the avian species can include Lapwings which can pose a problem around airports.

The inventors have found that a level of at least 3 ppm of the ergovaline alkaloid compound is sufficient to cause a deterrent effect. Preferably, the ergovaline may be present in a range from 3 ppm to 100 ppm.

Preferably, the endophyte may also confer resistance to the combination against biotic and abiotic stresses.

In preferred embodiments, biotic stresses include resistance to attack from insects and pests, including resistance to Grass Grub, (*Costelytra zealandica*) Argentine Stem Weevil (*Listronotus bonariensis*) and sucking insects (for example aphids of the *Rhopalosiphum padi* species.

In preferred embodiments, abiotic stresses include resistance to drought or dry periods as well as resistance to high or low temperature climates.

The inventors have found that by selecting an endophyte that also produces peramine and loline alkaloids, the grass cultivar may not only deter avian species, but also have a high tolerance to biotic and abiotic stresses. This is particularly advantageous in locations where the grass is subject to little care and attention and where the grass is not likely to be grazed by animals, such as grass adjacent an airport or other areas where birds are attracted to, for example areas where plant predatory insects are formed.

Preferably, the endophyte may also produce peramine alkaloids compounds within at least a portion of the cultivar herbage and seeds produced therefrom. Preferably, the peramine alkaloid may be present in a range from 1 ppm to 100 ppm or more. More preferably, the peramine alkaloid may be present at level of at least 1 ppm.

Preferably, the endophyte may also produce loline alkaloids within at least a portion of the cultivar herbage and seeds produced therefrom. Preferably, the loline alkaloid may be present in a range from 1 ppm to 9500 ppm or more. More preferably, the loline alkaloid may be present at level of at least 1500 ppm.

Preferably, the endophyte may also produce lolitrem alkaloids compounds within at least a portion of the cultivar herbage and seeds produced therefrom. Preferably, the lolitrem alkaloid may be present in a range from 1 ppm to 50 ppm or more. More preferably, the lolitrem alkaloid may be present at level of at least 1 ppm.

According to a further aspect of the present invention, there is provided a use of an endophyte and grass cultivar combination that repels avian species from the combination, characterised in that the endophyte in the combination produces ergovaline alkaloid compound sufficient to repel the avian species from the cultivar herbage and seeds produced therefrom.

According to a further aspect of the present invention, there is provided a use of an endophyte and grass cultivar combination including an endophyte selected from the group consisting of: AR601, AR602, AR603, AR604, AR4, AR5, AR8 and AR94 (Deposit Nos. V07/029058, V07/029059, V07/029060, V07/029061, V07/029054, V07/029055, V07/029056, V07/029057, and combinations thereof; characterised in that avian species are repelled from the cultivar herbage and seeds produced therefrom.

According to a further aspect of the present invention, there is provided a use of an endophyte and a *Festuca* grass cultivar combination, or grass cultivars exemplified by *Festuca* characteristics, that repels avian species from the combination, characterised in that the endophyte in the combination produces a level of at least 3 ppm of ergovaline alkaloid compound within a portion of the cultivar herbage and seeds produced therefrom.

According to a further aspect of the present invention, there is provided a use of an endophyte and a *Lolium* grass cultivar combination, or grass cultivars exemplified by *Lolium* characteristics, that repels avian species from the combination, characterised in that the endophyte in the combination produces a level of at least 3 ppm of ergovaline alkaloid compound within a portion of the cultivar herbage and seeds produced therefrom.

According to a further aspect of the present invention, there is provided a method of repelling avian species from an area of land by planting an endophyte and grass cultivar on or adjacent the land from which the avian species are to be repelled from characterised in that the endophyte in the combination produces ergovaline alkaloid compound sufficient to repel the avian species from the cultivar herbage and seeds produced therefrom.

According to a further aspect of the present invention, there is provided a method of repelling avian species from an area of land by planting an endophyte and grass cultivar on or adjacent the land from which the avian species are to be repelled from characterised in that the endophyte and grass cultivar combination including an endophyte selected from the group consisting of: AR601, AR602, AR603, AR604, AR4, AR5, AR8, AR94 (Deposit Nos. V07/029058, V07/029059, V07/029060, V07/029061, V07/029054, V07/029055, V07/029056, V07/029057, and combinations thereof; characterised in that avian species are repelled from the cultivar herbage and seeds produced therefrom.

According to a further aspect of the present invention, there is provided a method of repelling avian species from an area of land by planting an endophyte and Festuca grass cultivar or grass cultivars exemplified by Festuca characteristics, on or adjacent the land from which the avian species are to be repelled from characterised in that the endophyte in the combination produces a level of at least 3 ppm of ergovaline alkaloid compound within a portion of the cultivar herbage and seeds produced therefrom.

According to a further aspect of the present invention, there is provided a method of repelling avian species from an area of land by planting an endophyte and *Lolium* grass cultivar or grass cultivars exemplified by *Lolium* characteristics, on or adjacent the land from which the avian species are to be repelled from characterised in that the endophyte in the combination produces a level of at least 3 ppm of ergovaline alkaloid compound within a portion of the cultivar herbage and seeds produced therefrom.

According to a further aspect of the present invention, there is provided a method of screening an endophyte and grass cultivar combination, for the combinations ability to repel avian species by the steps of:
(a) cultivating the combination;
(b) measuring the level of an ergovaline alkaloid in the cultivated combination; and;
(c) selecting the combination if the level of ergovaline is above at least 3 ppm.

According to a further aspect of the present invention, there is provided a method of screening an endophyte and grass cultivar combination, for the combinations ability to repel avian species by the steps of:
(a) cultivating the combination;
(b) measuring the level of an ergovaline alkaloid in the cultivated combination; and;
(c) selecting the combination if the level of ergovaline is above at least 3 ppm; characterised in that the endophyte in the combination endophyte selected from the group consisting of: AR601, AR602, AR603, AR604, AR94 and AR4, AR5, AR8 (Deposit Nos. V07/029058, V07/029059, V07/029060, V07/029061, V07/029057, V07/029054, V07/029055, V07/029056), and combinations thereof.

According to a further aspect of the present invention, there is provided a method of screening an endophyte and *Festuca* grass cultivar combination, or grass cultivars exemplified by *Festuca* characteristics, for the combinations ability to repel avian species by the steps of:
(a) cultivating the combination;
(b) measuring the level of an ergovaline alkaloid in the cultivated combination; and;
(c) selecting the combination if the level of ergovaline is above at least 3 ppm.

According to a further aspect of the present invention, there is provided a method of screening an endophyte and *Lolium* grass cultivar combination, or grass cultivars exemplified by *Lolium* characteristics, for the combinations ability to repel avian species by the steps of:
(a) cultivating the combination;
(b) measuring the level of an ergovaline alkaloid in the cultivated combination; and;
(c) selecting the combination if the level of ergovaline is above at least 3 ppm.

It should be appreciated from the above description that there is provided a method of selecting and using an endophyte to repel birds from the grass and endophyte combination or area on which the combination grows. Embodiments of the invention not only provide identification of specific endophytes that confer repellent properties but also describe methods to select new endophytes for use as a repellent. Embodiments of the present invention provide methods to overcome difficulties in previous studies which allude to an endophyte and grass combination having a repellent effect but which use wild type endophyte and do not provide any guidance on methods of selection and key characteristics needed in a commercial product.

DETAILED DESCRIPTION OF THE PREFERRED EMBODIMENTS

Figure 1:
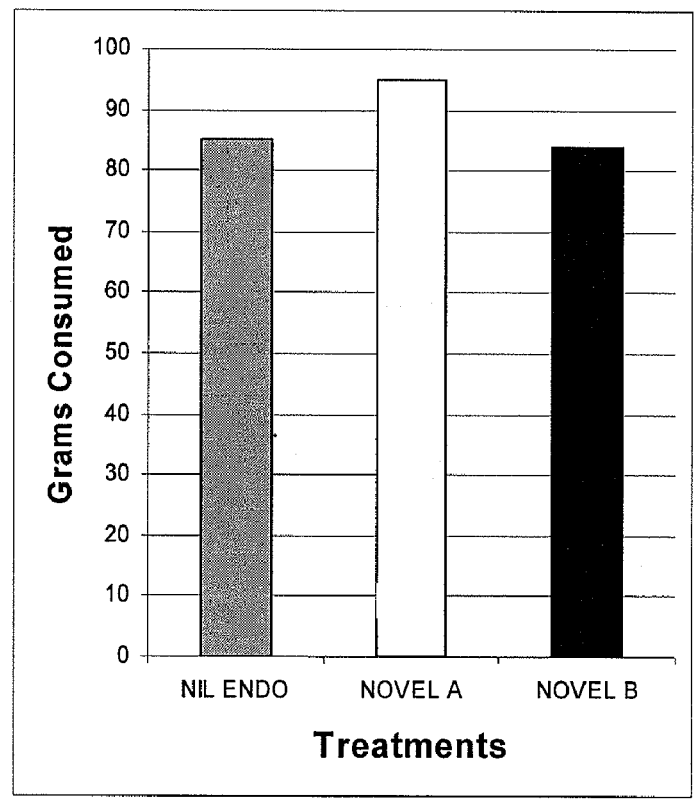
FIG. 1 is a bar chart that illustrates the percentage of seeds of different endophyte treatment consumed by 'naïve geese' in a feeding experiment.

Embodiments of the present invention relate to a grass based avian deterrent. More specifically, the invention relates to a grass cultivar and endophyte combination that produces alkaloid toxins sufficient to deter avian species from the grass cultivar and endophyte combination. As mentioned above, various primary and secondary deterrence methods have been attempted. However, a need exists for improved deterrence methods.

One secondary deterrent method is a repellence created via the food source of birds inducing a "post digestion feed back" (PDF) response. In feeling ill, the bird, through education and memory, avoids the earlier feeding area. PDF, as described by Conover et al. (Feeding Preferences and Changes in Mass of Canada Geese Grazig Endophyte-Infected Tall fescue, *The Condor* 98:859-862 (1996), incorporated herein by reference in its entirety) is the deterrent effect resulting from an animal eating something that is not initially associated with tastes but causes malaise over time and can affect the animals' long term food preference.

Studies have documented the PDF responses in geese and other pests. For example, a report published by The Berryman Institute (Gosser et al, Managing Problems Caused by Urban Canada Geese, *Berryman Institute Publication* 13, Utah State University, Logan (1997), incorporated herein by reference in its entirety) describes methods for deterring Canadian geese by planting grass that is less palatable to the geese, therefore discouraging the geese from feeding. The report describes that geese dislike tall fescue grasses, specifically the Kentucky-31 (K-31) cultivar, as the grass cultivar contains endophytes which produce toxic alkaloids that cause the PDF repellent effect. The report illustrates the PDF effect in relation to the K-31 variety but does not consider what particular endophytes cause this effect or the way the effect is achieved.

Durham et al. (Effect of endophyte consumption on food intake, growth and reproduction in praire voles, *Canadian Journal of Zoology* 76:960-969 (1998), incorporated herein by reference in its entirety) describes the use of endophyte infected grass seeds to cause a repellent effect in rodents. Durham et al., 1998 showed that over a number of 'learning experiments', vole rodents avoid consuming the endophyte infected tissue.

Conover et al. (Feeding Preferences and Changes in Mass of Canada Geese Grazig Endophyte-Infected Tall fescue, *The Condor* 98:859-862 (1996)) describes a study where Canadian geese fed K-31 tall fescue grass in a choice situation showed over time a preference to K-31 without endophyte present.

The above studies show a link between endophytes and animal deterrent, but no further details on this effect have been found. For example, there is no teaching as to what alkaloids cause the deterrent effect and how the deterrent effect can be maximised. Further, none of the studies discuss or mention other grass cultivars and/or endophyte combinations other than the use of K-31, which had been naturally infected with the endophyte *Acremonium coenophialum* (later reclassified as Neotyphodium coenophialum). Given the varying habitats and climates where bird problems are prevalent and the K-31 characteristics, K-31 infected with *N. coenophialum* is unlikely to be the most suitable grass cultivar or endophyte combination to use in all habitats and climates.

Fungal endophytes of the genus *Neotyphodium* infect a number of temperate climate Pooideae grasses. The *Neotyphodium* endophytes can produce alkaloids such as ergovaline, peramine and lolines which are considered to confer degrees of pest and disease protection upon the plants in which they naturally occur. U.S. Pat. Nos. 6,111,170 and 6,072,107 provide further background on grass and endophyte combinations and are each incorporated herein by reference in its entirety.

Embodiments of the instant invention relate to controlling and selecting an endophyte and grass combination to maximise the deterrent effect, where the combination is also suitable for varying habitats and climates. Some embodiments relate to methods that can be used to develop a robust grass and endophyte combination that is well understood, and a selection method that can be used to select combinations that are useful in a variety of habitats and climates.

Preferred embodiments of the present invention are now explained in more detail using examples below. In these experiments, the inventors show that a bird post digestive feedback (PDF) reaction occurs as measured by the learned behaviour observed.

1. Target Avian Species: Canadian Geese (*Branta canadensis*)

As described in Examples 1-4, approximately 50 geese were obtained from the wild. The geese were wing clipped and contained in a fenced off area to become familiar with their surroundings with little human contact. No endophytic material, either in seed or forage, was fed to these geese for a period of three weeks. Body weights were maintained with feed of crushed barley and Timothy grass forage. The geese were then split into various groups, for the two trials assessing the PDF response to inoculated endophyte seed (Example 1) and inoculated endophyte herbage (Example 2).

EXAMPLE 1

Seed, Cafeteria Choice Trial

The inventors ran a series of 'cafeteria choice trials' where the gaggle of approximately 20 geese chose between (i) seed without endophyte infection (Nil-endophyte); or (ii) seed that had been inoculated with endophyte A; or (iii) seed that had been inoculated with endophyte B. This tested the PDF and learnt behaviour of post digestion feed back in geese in seed feeding trials.

Seed and Endophyte Combinations Tested

Three different seed and endophyte combinations were tested during this experiment. The seed from the perennial ryegrass cultivar, Kingston, was inoculated with either endophyte A (Wild Type) or with endophyte B (Endosafe AR5).

Therefore, the three different seed and endophyte combinations that were tested consisted of:

(i) Kingston seed without endophyte (Nil-Endophyte);
(ii) Kingston seed inoculated with Endophyte A (Wild type endophyte); and
(iii) Greenstone seed inoculated with Endophyte B (AR 5 endophyte).

Run 1—Day 1;

The seed was distributed in trays that were designed so only the head and necks of the geese could reach the food source. During the trials, the geese were feed a selection of 500 g from each of the seed selections, as notes above in points (i) to (iii) above.

The amount of test seed consumed during the trials was determined by weighting the trays and determining the amount of remaining seed after a two hour feeding period. At the end of this first run, the geese consumed the majority of the seed from each selection. No trends between each of the three selections were shown towards one type or another. As shown in FIG. 1, this group of naïve geese consumed the majority of the seed from each feeding station.

Figure 2:
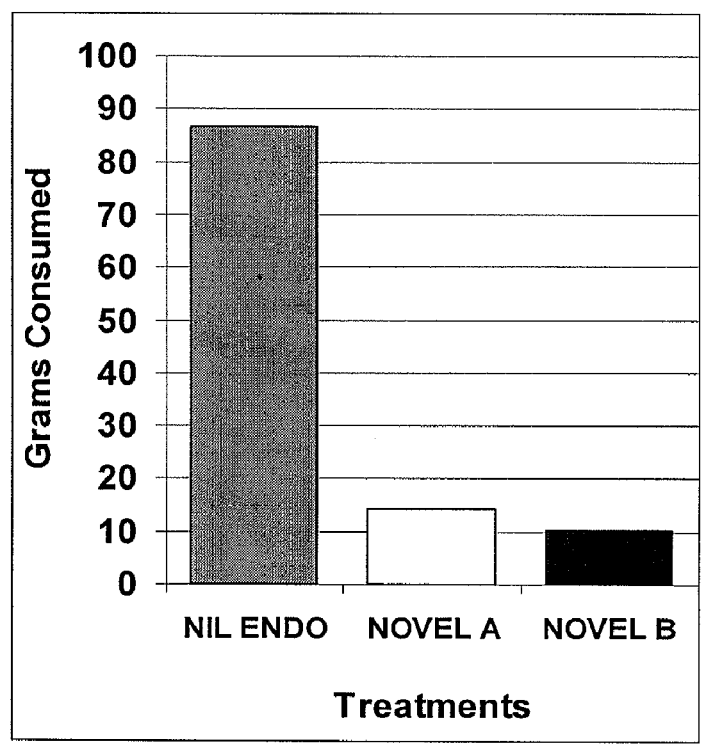
FIG. 2 is a bar chart that illustrates the percentage of seeds of different endophyte treatment consumed by 'learned geese' in a feeding experiment.

Run 2—Five Days later;

The trial in Run 1 above was then repeated each day over a period of five days. It was observed that between the beginning of the trials to the end of the five days in Run 2, the geese in the trials 'learned' from their feeding experiences and consumed all of the 'nil' endophyte seed and approximately 10% of the seed from the Endophyte A and B feeding stations. The total percentage of seed consumed from each feeding station is shown in the graph in FIG. 2. This showed that a PDF effect had occurred and that the endophyte and grass combination exhibited a repellent effect.

Run 3—Learned Geese, Three Months Later;

The inventors then conducted a further trial subsequent to Runs 1 and 2. The learned geese from the Runs 1 and 2, who had been exposed to endophyte and had displayed PDF behaviour were removed from the trial and fed on a high maintenance nil endophyte diet of timothy forage grass and crushed barley for three months.

Following this three month exposure to the nil endophyte grass, these learned geese were then exposed to feeding stations containing endophyte infected seed or nil-endophyte infected seed. At the same time, in a separate enclosure, a trial was conducted with naïve geese also being exposed to feeding stations containing endophyte infected seed or nil-endophyte infected seed.

Figure 3:
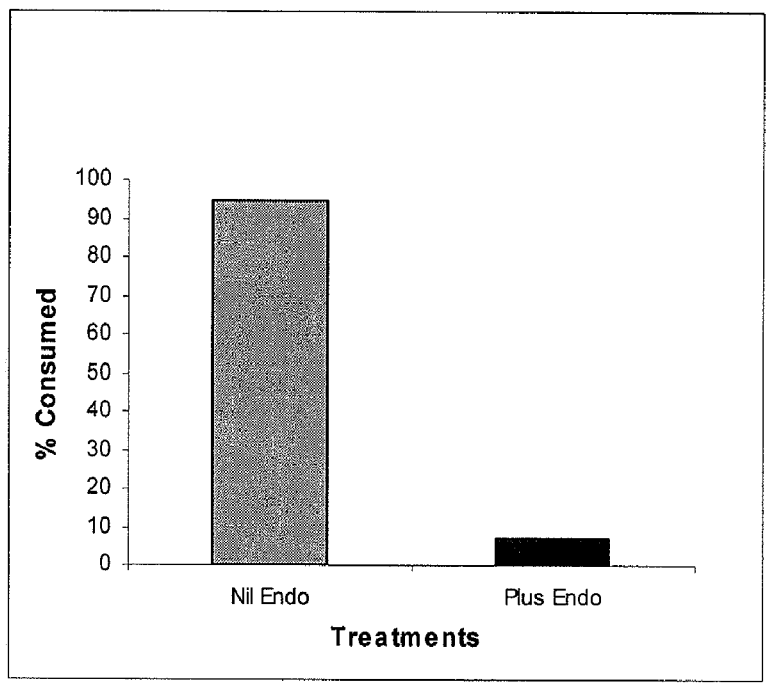
FIG. 3 is a bar chart that illustrates the percentage of seeds of different endophyte treatment consumed by 'learned geese' in a feeding experiment conducted after 3 months from the initial learning feeding.

The graph in FIG. 3 shows the consumption rate of the learned geese from this run. As shown, the percentage of nil-endophyte infected seed consumed was approximately 95% whereas the percentage of endophyte infected seed consumed was only approximately 5%. Again, this Run showed that the grass and endophyte combination exhibited a repellent effect and that the geese retained the PDF learned behaviour over the 3 month time period. In practice, this illustrates that birds are not only repelled in the short term by the endophyte and grass combination but that the endophyte and grass combination also provide a longer term repellence solution.

EXAMPLE 2

Herbage, Choice Trial

In this trial, the methodology used was of similar manner to that of Example 1. The main difference in this trial was that the geese were fed on herbage rather than seeds.

During this trial, 20 naïve geese that had no exposure to any endophytes were confined to an area of an approximate size of 15 m$^2$. Within this area, perennial ryegrass herbage known as 'Grasslands Nui' (Nui) was grown and random sections (of an approximate size of 0.5 m²) of the grass were either infected with AR1 endophyte or not infected at all (nil-endophyte). Each of these plots was randomly distributed within the larger area and cut to ground level.

Figure 4:
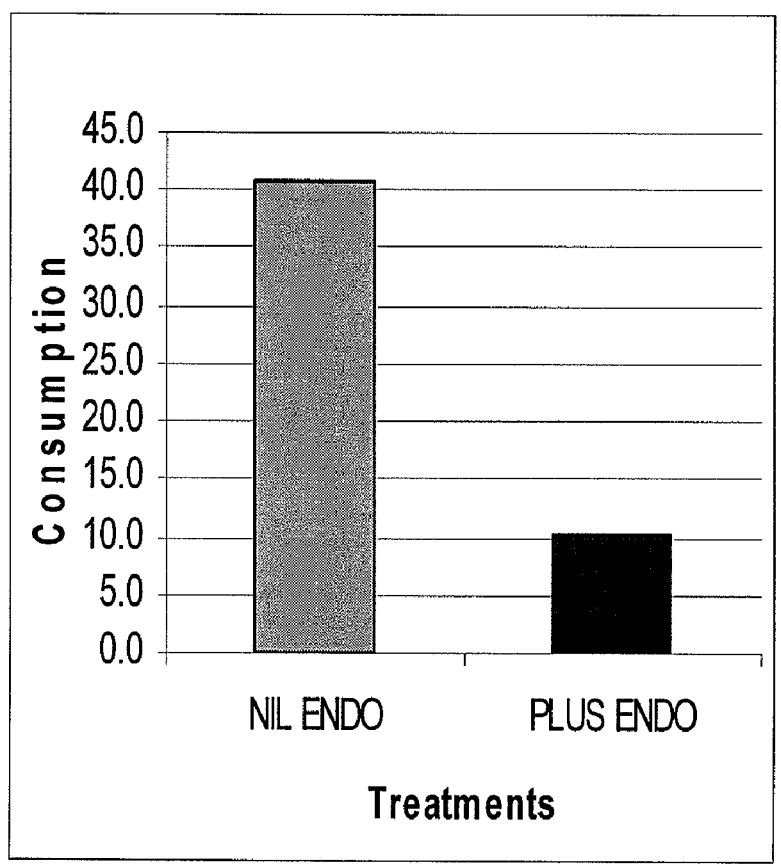
FIG. 4 is a bar chart that illustrates the amount in grams of herbage consumed in a further feeding experiment of 'learned geese'.

The geese were exposed to a number of areas of the same approximate size as detailed above and were only moved when the grass levels where significantly reduced or fouled. After 10 days of geese exposure to the grass areas, the amount of herbage consumed was assessed. As shown in the graph of FIG. 4, the geese consumed approximately 40.0 g of non-infected 'nil' endophyte grass herbage and approximately 10.0 g of the endophyte infected grass. This shows that the geese had developed a grazing preference within this time period and developed PDF behaviour, even when exposed to a different portion of the plant. This also illustrates that the repellent effect results from alkaloid toxins throughout the herbage and not just from the seed.

EXAMPLE 3

Herbage, NO Choice Trial

A similar trial as described in Example 2 was conducted to assess the amount of herbage a gaggle of geese would consume when the geese were put onto a no-choice diet.

In this trial, two groups of four naïve geese were confined to cages of 1 m by 3.5 m. The geese were then put onto a diet of nil endophyte Nui ryegrass for a period of eight days. Following this, the geese were then moved to a section of Nui ryegrass that had been infected with AR1 endophyte, also for an eight day period. Post grazing samples of the amount of herbage consumed were taken and assessed.

Figure 5:
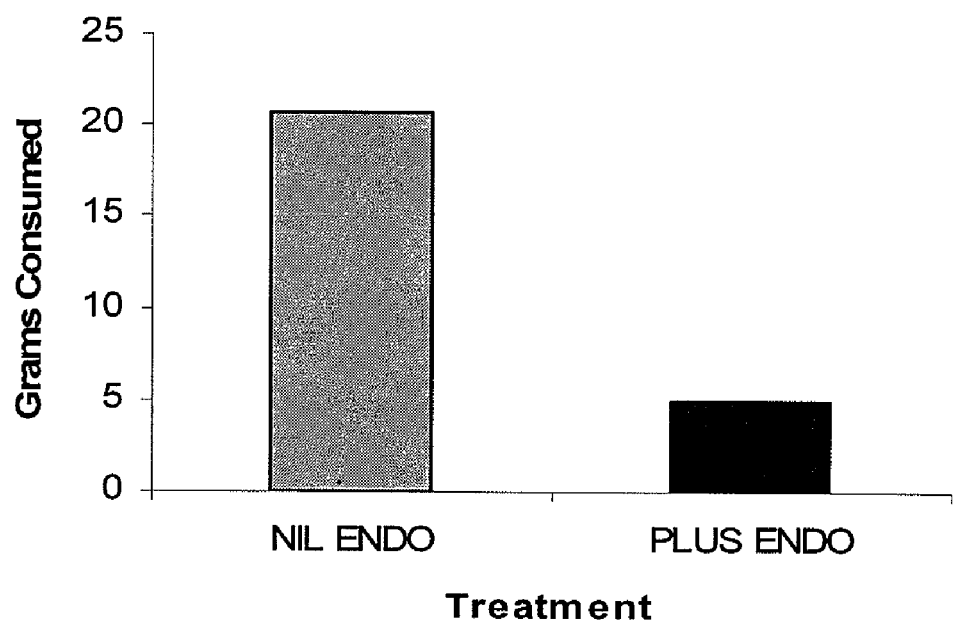
FIG. 5 is a bar chart that illustrates the average amount of plant material (dry weight) consumed by the geese per day in a no-choice feed experiment of nil endophyte infected plant material and endophyte infected plant material.
Figure 6:
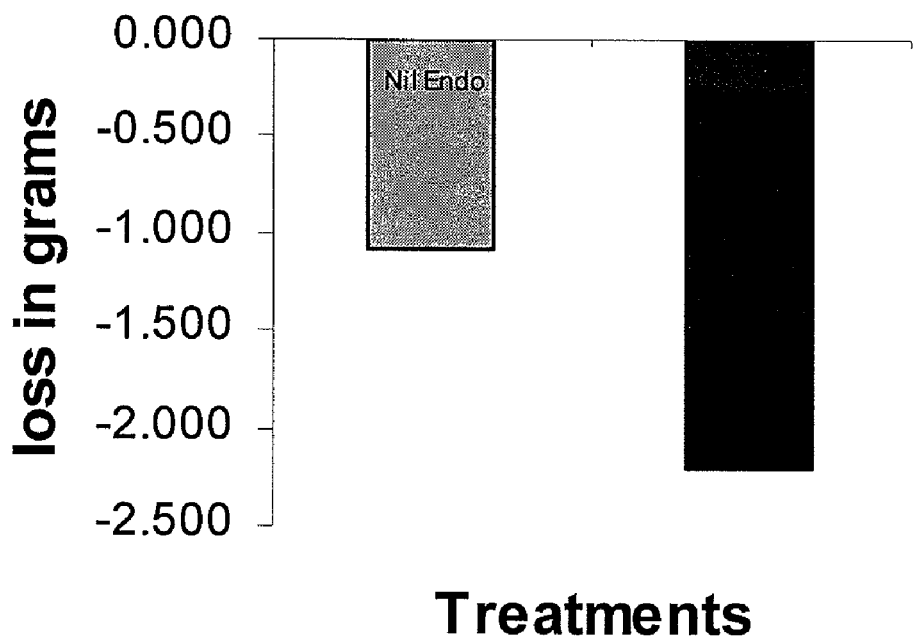
FIG. 6 is a bar chart that illustrates the amount of weight loss experienced by geese feeding on endophyte infected plant material.

As shown in FIG. 5 the average amount of dry weight consumed per day of plant material containing nil endophyte was approximately 20 g. This was in comparison to the 5 g of plant martial consumed that was infected with endophyte. Also shown in FIG. 6, during the eight-day consumption period on the endophyte infected plant material, the geese experienced a weight loss of approximately 2.2 g, while only approximately 1 g of weight was lost during the consumption period on nil-endophyte infected grass.

EXAMPLE 4

A further trial was then completed to assess geese feeding habits using seed collected from four different grass cultivars infected with endophyte to determine which grass cultivar(s) the geese preferred and hence which cultivars had the highest repellent effect.

The four different perennial ryegrass cultivars and hybrids (now referred herein as 'ryegrass') (and control) that were tested include the following:
 (i) Grass seed with no endophyte infection (control);
 (ii) Nui cultivar infected with AR1 endophyte;
 (iii) Kingston cultivar infected with wild type endophyte;
 (iv) 'Grasslands Greenstone' (Greenstone) cultivar infected with Endosafe®; and,
 (v) Aries HD cultivar infected with wild type endophyte.

The trials were conducted in a similar manner as previously outlined above in Example 1. Here the feeding preferences of 20 naïve geese of seed from 5 different grass cultivars and endophyte infection were assessed. The amount of seed consumed by the geese was assessed over a time period of three hours after distributing the seed. This trial ran for three days, with the seed being distributed once a day.

Figure 7:
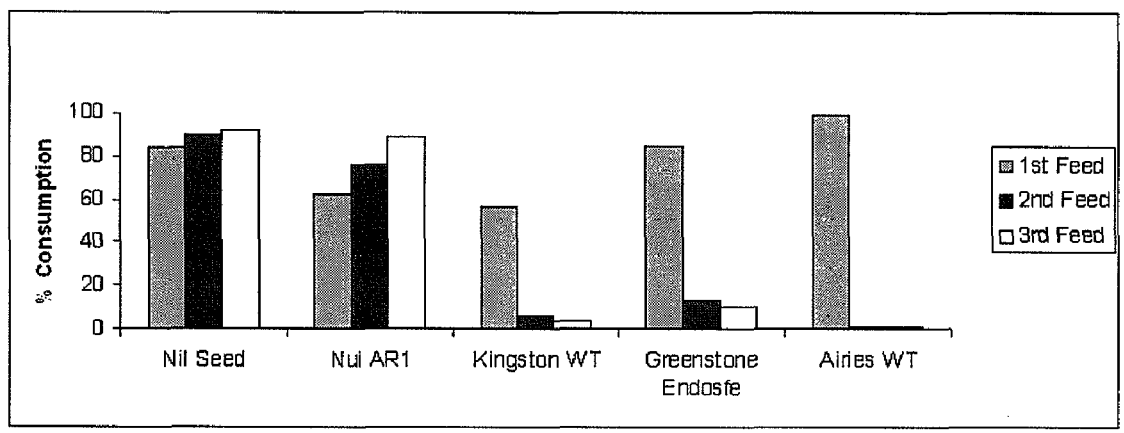
FIG. 7 is a bar chart that illustrates the percentage of seed from five different grass and endophyte cultivars consumed in three different feeding sessions, by the same group of geese.

The results of this trial are shown in FIG. 7. As shown, during the first feeding session, a high percentage (from 60% to 100%) of the seed from all five different feeding stations was consumed. During the second and third feeding sessions, there was a sharp decrease in the percentage of seed consumed from three out of the five combinations offered to the geese. For example, the percentage of Kingston cultivar seed consumed dropped from a 60% consumption rate in the first feed to an approximately 5% consumption in the second and third feeding sessions. Greenstone cultivar consumption dropped from 80% consumption in the first feeding session to 10% consumption in the second and third feeding sessions. Airies cultivar went from a 100% consumption rate to an approximately 2% consumption rate in the second and third feeding sessions.

2. Alkaloid Concentration Analysis

From the above results the inventors concluded that the degree of repellence was based on the level of one or more alkaloids in the combination causing the PDF response behaviour, as described in Examples 5-8.

EXAMPLE 5

To verify the above findings, the inventors conducted a further trial to assess the alkaloid concentrations of each grass cultivar to assess if there was a common alkaloid between the grass cultivars.

Figure 8:
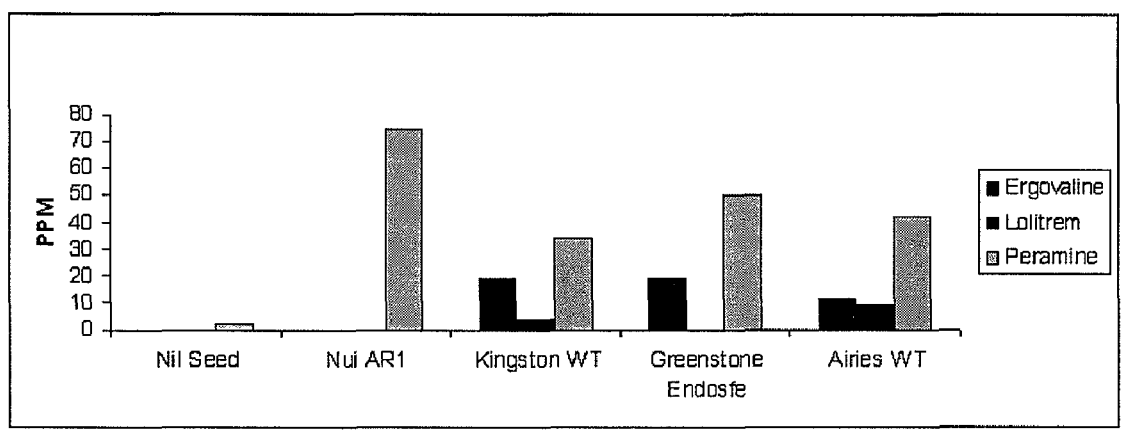
FIG. 8 is a bar chart that illustrates the alkaloid levels of three different alkaloids, ergovaline, lolitrem and peramine from four grass and endophyte cultivars against a nil endophyte seed.

FIG. 8 shows the content of three alkaloids, ergovaline, lolitrem and peramine from the five different grass cultivars tested in Example 3. From these results, the combinations that exhibited the strongest PDF responses had high levels of the alkaloid ergovaline. As shown, of the cultivars that displayed the PDF responses, Airies had a 10 ppm concentration of ergovaline while Greenstone and Kingstone had a 20 ppm concentration. In comparison, the combinations that did not display the PDF response effect, specifically the 'nil' infected seed and Nui, had no ergovaline present.

There was no clear pattern from the results observed for other alkaloids. For example, Kingstone and Airies both had small concentration levels of lolitrem, while Greenstone had no detectable levels of lolitrem. Levels of peramine alkaloid were observed in all grass cultivars, including the 'nil' infected seed and the Nui cultivar, hence it is concluded that peramine or lolitrem was not a cause of the exhibited PDF response.

EXAMPLE 6

Given the above results, further trials were completed to select preferred candidates of endophyte and grass cultivar that maximised ergovaline levels. Selections were also made based on alkaloid levels being exhibited throughout the herbage of the plant, rather than just those levels concentrated within a particular area. A further selection criteria was to screen for levels of peramine and loline alkaloids which are known to confer resistance to biotic and abiotic stresses.

Alkaloid Concentration—Tall Fescue

Ergovaline Concentration

Figure 9:
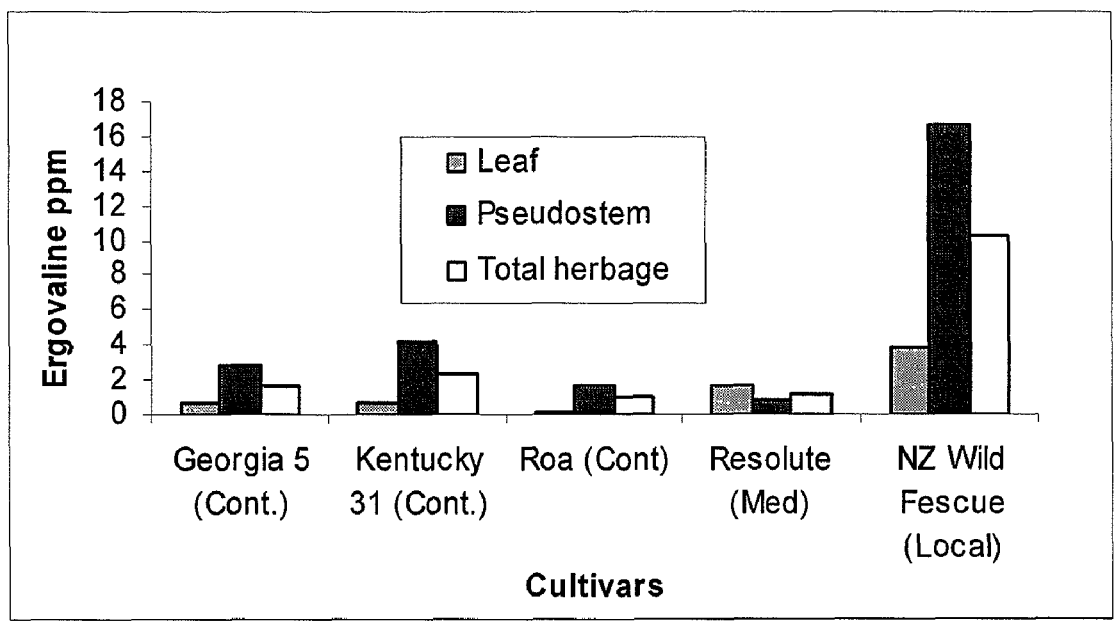
FIG. 9 is a bar chart that illustrates ergovaline concentration in different cultivars infected with the same wild type endophyte strain.

Firstly, the inventors assessed the alkaloid, ergovaline, in different tall fescue grass cultivars infected with the same New Zealand wild endophyte strain. The inventors assessed the concentration of ergovaline throughout the total herbage of the plant, as well as throughout the leaf and pseudostem. The results of this assessment are shown in FIG. 9. As shown in FIG. 9, ergovaline expression in New Zealand wild fescue was the highest of the grass cultivars tested.

Leaf Colonisation

Figure 10:
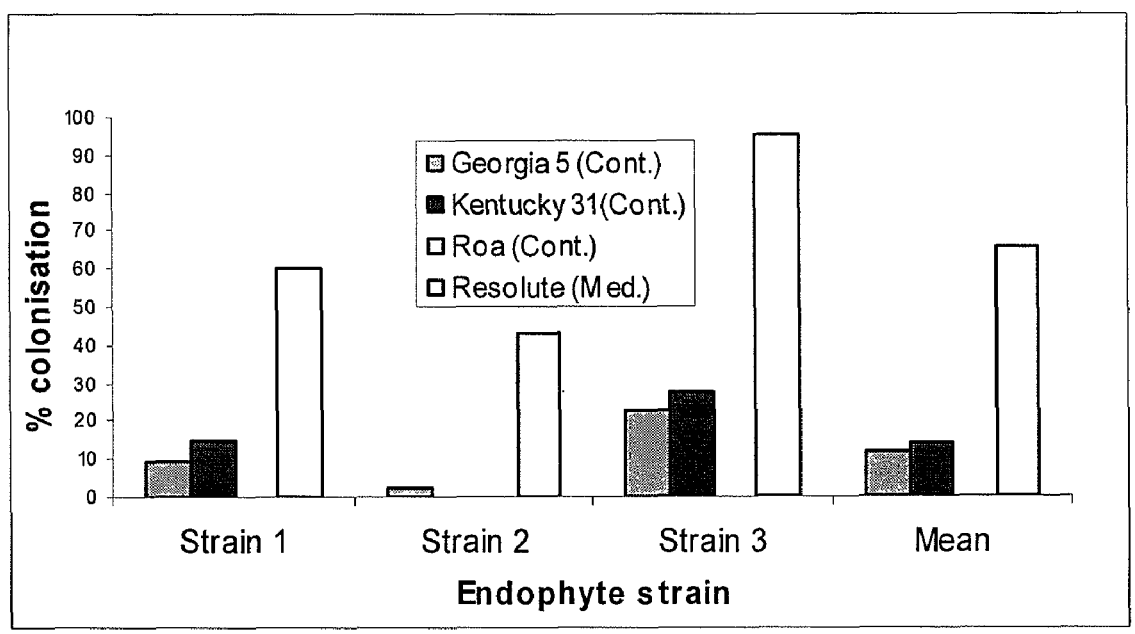
FIG. 10 is a bar chart that illustrates the differences of leaf colonisation of four different tall fescue cultivars infected with three different endophyte strains.

The inventors then assessed the percentage of leaf colonisation of three New Zealand wild tall fescue endophyte strains in four tall fescue cultivars. The results of this assessment are shown in FIG. 10. Here, the grass cultivar Resolute showed a high percentage of leaf colonisation overall between all three endophyte strains and all the grass cultivars assessed.

Alkaloid Concentration—*Lolium* Species

Peramine Alkaloid

The alkaloid, peramine has been shown to have an increased effect in pest resistance, such as insects. Therefore, this is also a further preferred characteristic of a grass and endophyte combination.

To assess the peramine expression within particular ryegrass specific endophyte strains in one ryegrass cultivar, using High Performance Liquid Chromatography (HPLC), the inventors assessed the peramine expression in both the leaf and pseudostem from six different endophyte strains (AR41, AR5, AR8, AR4 and AR9001 in combination with the same ryegrass cultivar.

Figure 11:
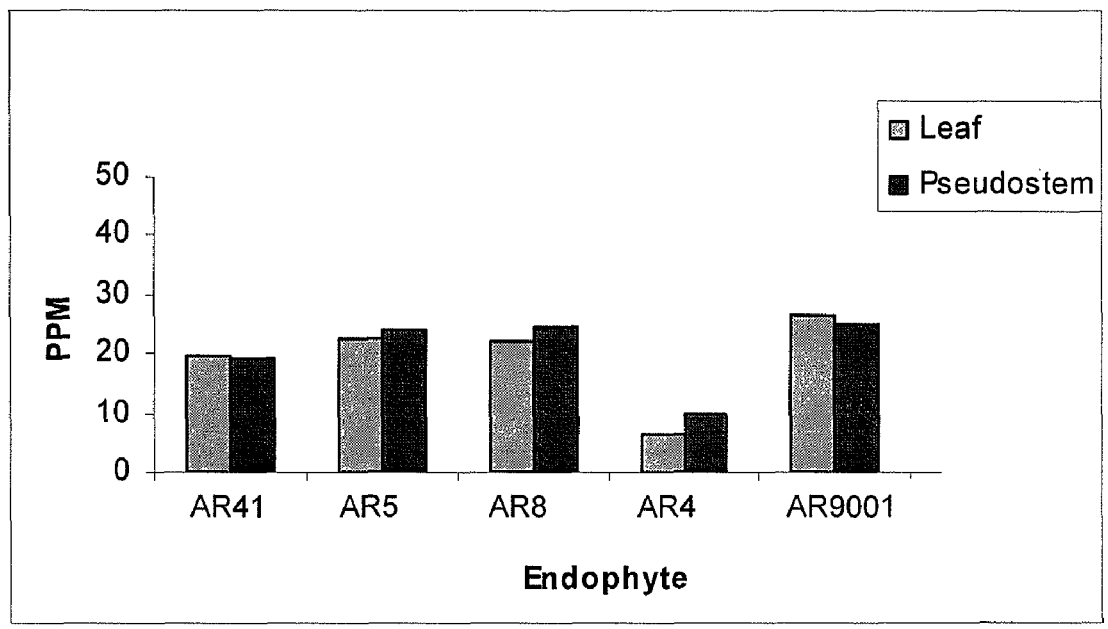
FIG. 11 is a bar chart that illustrates peramine expression in six different ryegrass endophyte strains in the same ryegrass cultivar.

As shown in FIG. 11, the majority of the endophytes displayed a peramine concentration level of approximately 20 ppm in both the leaf and the pseudostem. In particular, the combination with the Waiau endophyte displayed the highest peramine concentration of 35 ppm and 40 ppm in the leaf and pseudostem respectively.

Ergovaline Alkaloid

As previously discussed, trial results illustrated that ergovaline is an important alkaloid in producing the PDF response displayed by the geese (Example 5). Therefore, it is preferable to have a high concentration of this alkaloid within the herbage of grass and endophyte combination.

The inventors assessed the same endophyte strains as above (AR41, AR5, AR8, AR4 and AR9001 for the level of ergovaline concentration, in the same ryegrass cultivar.

Figure 12:
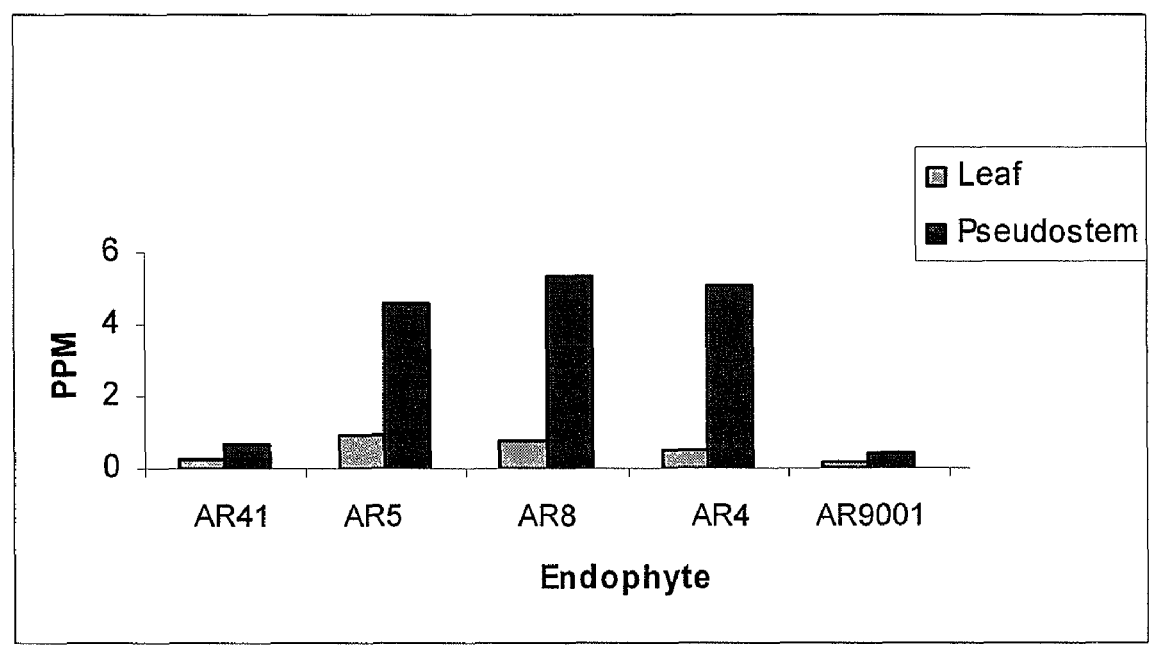
FIG. 12 is a bar chart that illustrates ergovaline expression in six different ryegrass endophyte strains (same to that in FIG. 11) in the same ryegrass cultivar.

FIG. 12 shows the ergovaline concentrations expressed within these ryegrass and endophyte combinations. Here, endophytes AR4, AR5, and AR8 displayed the highest concentration of ergovaline expression. The expression was greatest throughout the pseudostem; however, ergovaline expression was also displayed throughout the leaf.

The tests in this Example showed that endophytes AR5 and AR8 have high concentration levels of both the alkaloids ergovaline and peramine. Therefore, combinations with these endophytes can have high bird repellent properties as well as good resistance to biotic (insect) stresses. Endophyte AR4 can further provide a bird repelling cultivar, but as it expresses lower levels of peramine, is better suited to environments with fewer insect stresses.

Alkaloid Concentration—*Lolium* and *Festuca* Species

The inventors also assessed the degree of alkaloid expression (peramine, lolitrem and ergovaline) throughout the leaf and pseudostem from four different tall fescue endophytes (AR601, AR602, AR603 and unknown endophyte) infected in the same tall fescue cultivar and from one endophyte strain, AR94 infected in a ryegrass cultivar.

Figure 13:
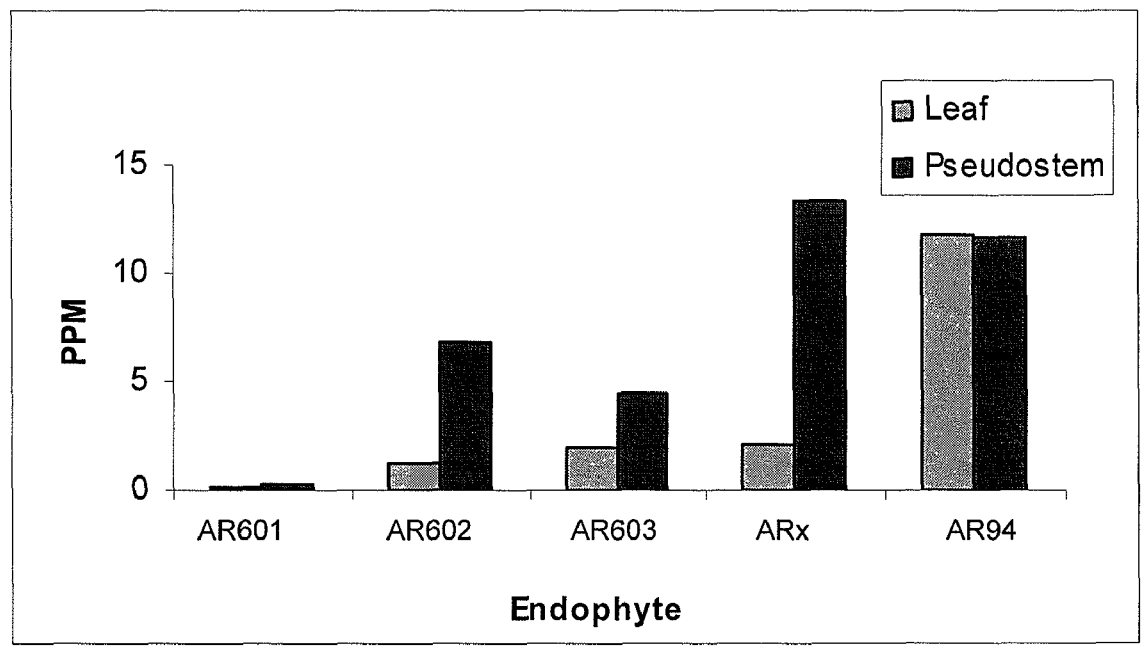
FIG. 13 is a bar chart that illustrates peramine expression in five different endophyte strains, four in tall fescue grass cultivars and one in a ryegrass cultivar.

As shown in FIG. 13, peramine expression in the unknown Nui endophyte and tall fescue cultivars was high (>10 ppm concentration) throughout the pseudostem of the cultivars.

The tall fescue and AR602 combination also produced high peramine expression, as did the ryegrass and AR94 combination.

Figure 14:
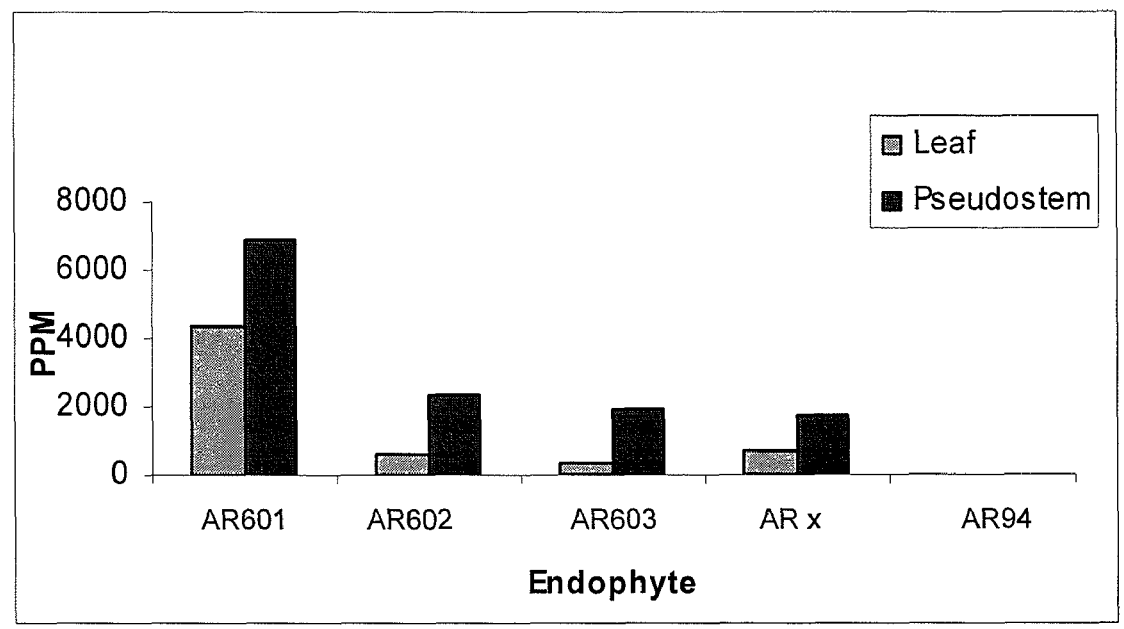
FIG. 14 is a bar chart that illustrates lolitrem expression in five different endophyte strains, four in tall fescue grass cultivars and one in a ryegrass cultivar.

FIG. 14 shows the expression of lolitrem alkaloid of the various endophyte and tall fescue/ryegrass cultivar combinations. As illustrated, tall fescue and AR601 combination showed a high expression of lolitrem concentration. Other tall fescue and endophyte combinations also displayed moderate levels of loline expression. By comparison, ryegrass and AR94 combination did not express any detectable loline alkaloids.

Figure 15:
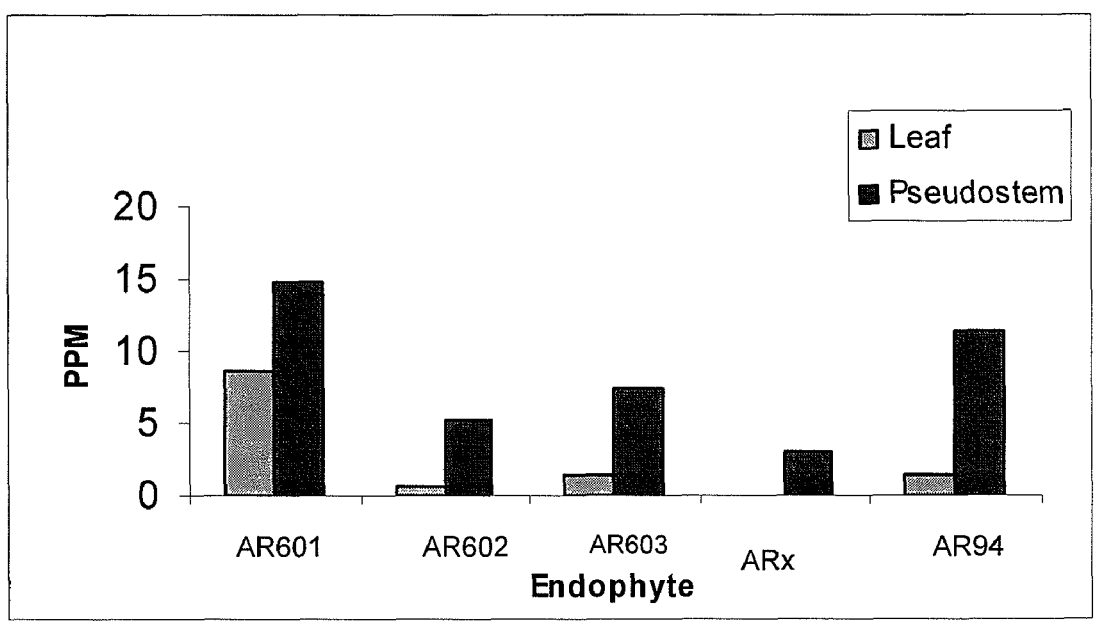
FIG. 15 is a bar chart that illustrates ergovaline expression in five different endophyte strains, four in tall fescue grass cultivars and one in a ryegrass cultivar.

FIG. 15 shows the concentration of ergovaline expression of grass and endophyte combinations as discussed above. As shown, the tall fescue and AR601 combination exhibited a high level of ergovaline concentration throughout the plant. There were comparatively high levels of ergovaline throughout the leaf and pseudostem. In comparison, the ryegrass and AR94 combination exhibited high levels of ergovaline expression in the pseudostem but with only a small amount within the leaf.

EXAMPLE 7

Further trials are conducted to select preferred candidates of endophyte and grass cultivar that maximise ergovaline levels. Selections are also made based on alkaloid levels being exhibited throughout the herbage of the plant, rather than just those levels concentrated within a particular area. A further selection criteria is to screen for levels of peramine and loline alkaloids which are known to confer resistance to biotic and abiotic stresses.

Ergovaline Concentration

Firstly, levels of the alkaloid ergovaline are assessed in different tall fescue grass cultivars infected with the same New Zealand wild endophyte strain. The concentration of ergovaline is also assessed throughout the total herbage of the plant, as well as throughout the leaf and pseudostem.

Leaf Colonisation

The percentage of leaf colonisation of three New Zealand wild tall fescue endophyte strains in four tall fescue cultivars is subsequently evaluated.

Alkaloid Concentration—Ryegrass

Peramine Alkaloid

The alkaloid, peramine has been shown to have an increased effect in pest resistance, such as insects. Therefore, this is also a further preferred characteristic of a grass and endophyte combination.

To assess the peramine expression within particular ryegrass specific endophyte strains in one perennial ryegrass cultivar, the level of peramine expression in both the leaf and pseudostem from different endophyte strains (AR4, AR5 and AR94), in combination with the same ryegrass cultivar, is evaluated. Expression levels of at least 15 ppm in the leaf and, or alternatively, in the pseudostem is detected.

Ergovaline Alkaloid

As previously discussed, trial results illustrated that ergovaline is an important alkaloid in producing the PDF response displayed by the geese (Example 5). Therefore, it is preferable to have a high concentration of this alkaloid within the herbage of grass and endophyte combination.

The same endophyte strains (AR4, AR5 and AR94) in combination with the ryegrass cultivar as described above are evaluated for the level of ergovaline concentration. Levels of ergovaline of at least 5 ppm, 10 ppm or 15 ppm within the endophyte and ryegrass combination are detected. The expression is greatest throughout the pseudostem; however, ergovaline expression is also displayed throughout the leaf.

Combinations with these endophytes can have high bird repellent properties as well as good resistance to biotic (insect) stresses.

Alkaloid Concentration—Perennial Ryegrass and Tall Fescue

The degree of alkaloid expression (peramine, lolitrem and ergovaline) throughout the leaf and pseudostem of different tall fescue endophytes (AR94, AR4, AR5, AR8) infected in the same tall fescue cultivar is assessed.

Peramine expression of at least 15 ppm concentration is detected throughout the pseudostem of the cultivars.

The expression of lolitrem alkaloid of the various endophyte and ryegrass cultivar combinations is evaluated. High expression of lolitrem concentration within the range of 1-50 ppm is detected in the combinations.

The concentration of ergovaline expression of grass and endophyte combinations as discussed above is evaluated. High levels of ergovaline concentration of at least 5 ppm, 10 ppm, or 15 ppm are detected throughout the plant in the various tall fescue and endophyte combinations and ryegrass and endophyte combinations. Comparatively high levels of ergovaline are found throughout the leaves and pseudostems of the combinations The combinations displaying the highest levels of ergovaline, peramine and/or lolitrem levels demonstrate efficacy in repelling avian species using protocols described in Examples 1-4.

It is found that by selecting an endophyte that produces peramine and lolitrem (in ryegrass) and loline (in fescue) alkaloids in addition to levels of ergovaline effective for repelling avian species, the grass not only deters avian species but also produces a high tolerance to biotic and abiotic stresses. This finding is also the case with ryegrass cultivars. Biotic stresses include resistance to attack from insects and pests. Specific examples include resistance to Grass Grub, (*Costelytra zealandica*) Argentine Stem Weevil (*Listronotus bonariensis*) and sucking insects such as, for example *Rhopalosiphum padi*. Abiotic stresses include resistance to drought or dry periods as well as resistance to high or low temperature climates. High temperatures include temperatures from 27° C. and above. For example, temperatures may include 27° C., 30° C., 32° C., 35° C. or 40° C. While low temperatures include any temperatures below, and including, 7° C., 5° C., 3° C. or 0° C. for example.

EXAMPLE 8

Tall Fescue Turf Cultivar "Jackal" Inoculated with AR601 and AR604

Following the above trials, the inventors assessed the further concentration of alkaloids in a tall fescue turf cultivar "Jackal" inoculated with AR601 & AR604 endophytes The alkaloid concentrations over a time period of approximately 1 year where assessed using the High Performance Liquid Chromatography (HPLC), methods described above.

Figure 16:
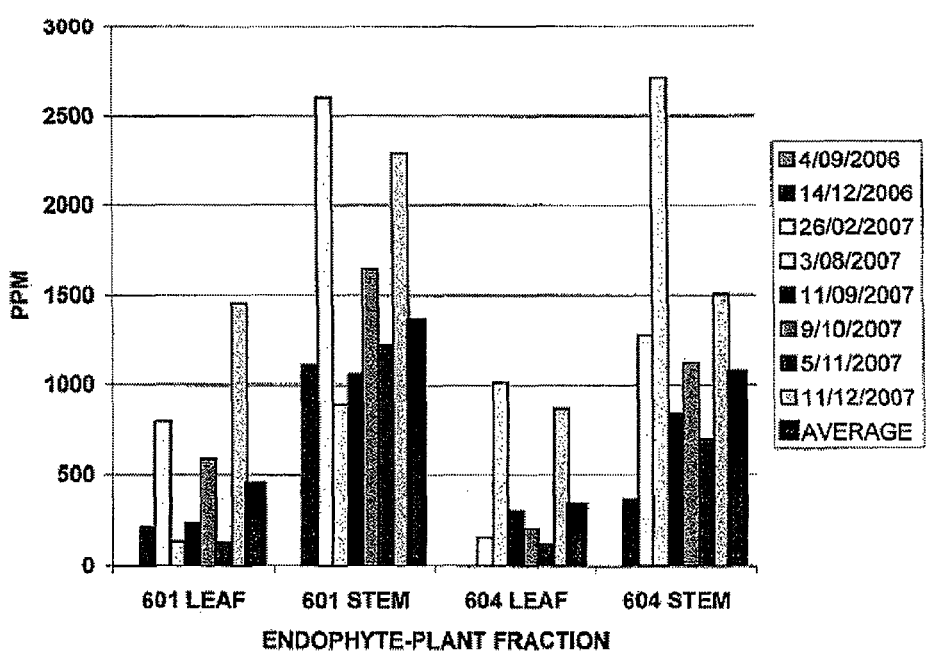
FIG. 16 is a bar chart that illustrates the concentration of ergovaline in various plant anatomy of "Jackal" grass cultivar inoculated with either AR601 or AR604.
Figure 17:
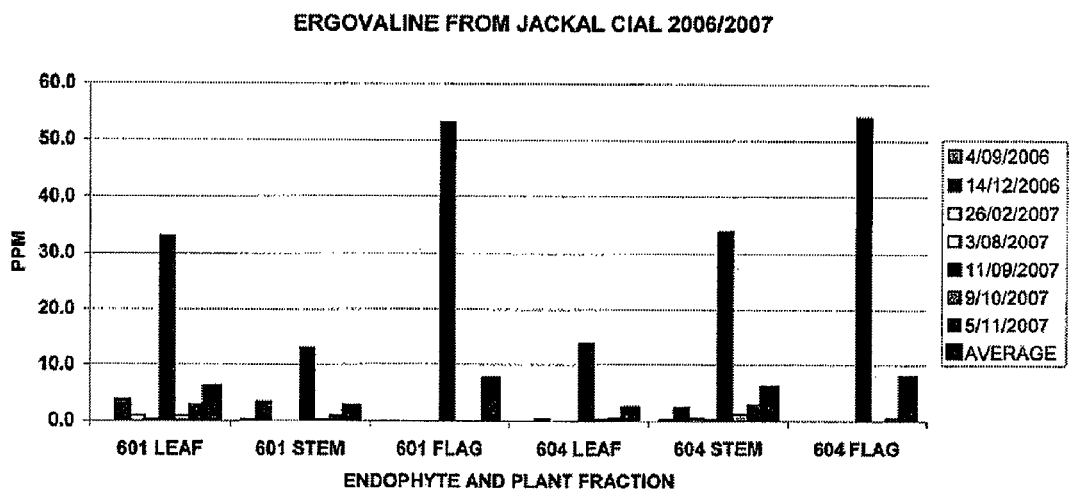
FIG. 17 is a bar chart that illustrates the concentration of lolines in various plant anatomy of "Jackal" grass cultivar inoculated with either AR601 or AR604.

FIGS. 16 and 17 show the results of the concentration analysis of the alkaloids lolines and ergovaline respectively from Jackal inoculated with either AR601 or AR604. Alkaloid measurements where taken from both the leaf and stem of the plants. As shown in the comparison, the stems of the plants had a higher alkaloid concentration. Additional seasonal variations can also be shown in the Figures.

TABLE 1

Shows the average alkaloid concentration in pseudostems of Jackal tall fescue infected with AR601 or AR604.

|  | Ergovaline (ppm) | Lolines (ppm) |
| --- | --- | --- |
| AR601 | 8.3 | 1816 |
| AR604 | 7.7 | 1778 |

3. Target Avian Species: Gulls (*Larus dominicus*)

The inventors conducted a further trial to determine the effect of introducing the repellent into an animal feed (pig feed) and determines the repellence effect on gulls (omnivorous birds), as described in the next example.

EXAMPLE 9

Treatments

To assess the PDF effect in gulls from endophytes the following treatments were assessed: (i) Commercially available pig pellets made from crushed grain or (ii) commercially available pig pellets externally hand-coated with ground powder produced from a ground endophytic seed.

To produce the ground endophytic seed for coating the pellets, 40 kg of endophyte-containing seed was commercially ground, with the temperature never exceeding 30 deg Celsius. The pellets were then manufactured by treating 20 kg lots of standard pig pellets with a 2 kg coating of ground seed powder in a concrete mixer, wherein the pellets were sprayed with warm water to produce a sticky surface that was then dusted with powder and allowed to air dry. Most of the pellets being coated ranged in size from 25 to 30 mm long by 15 mm diameter. Broken pellets smaller than 5 mm by 5 mm were also treated in the mix. A trial to confirm that the birds would not reject pellets containing the endophyte powder was conducted eight weeks prior to the trial and no rejection was noted.

Run 1

Observation of Gulls Behaviour Prior to Testing

Observation of the birds flocking to the pig farm at feeding times showed two distinct groups of birds that, when finished with opportunistic feeding for the day, loitered at specific locations post-feeding. These post-feeding locations were on bare, raised stony paddocks that offer security and good vision.

Pre-Trial Manipulating of the Gulls Feeding Habits

Each day for three weeks, the gulls were fed 50 kg of untreated pig pellets per day in the mornings at one of these loitering areas. The gulls appeared to consume all that was offered to them. The area was fenced off from the pigs.

During this pre-trial behaviour manipulation, the birds learned that there was regular feeding at this area and consumed the pig feed on most fine days through the three week pre-feeding period. On inspection in the mornings the birds were not in these rest areas but actively feeding from troughs around the whole farm by following the feed carts for opportunistic feeding. Once these troughs were emptied by the communal feeding, the gulls spent the rest of the day in these rest areas and were observed there until disturbed in the evenings. Gulls were observed to swallow the pellets whole.

Trial

At the end of the three week pre-feeding time period, the trial testing above treatments commenced. Each morning, pellets treated as described were placed into separate troughs that were located in this fenced off area. The trough and pellets were weighed before feeding in order to measure the amount of pellets consumed the following morning.

For 15 days, the troughs were measured for daily consumption. During this period, it was noticed that there was some rejection of the smaller treated pellets. Visual observations of the treated pellets consumed showed a marked preference by the gulls in consuming whole large pellets rather than the broken smaller pieces.

Results

On day 1, the birds consumed less endophyte treated pellets. This demonstrates that the birds were able to detect differences by indicators such as, smell, taste or visual differences between the troughs containing untreated and treated pellets. However, there was no total rejection from the onset.

Figure 18:
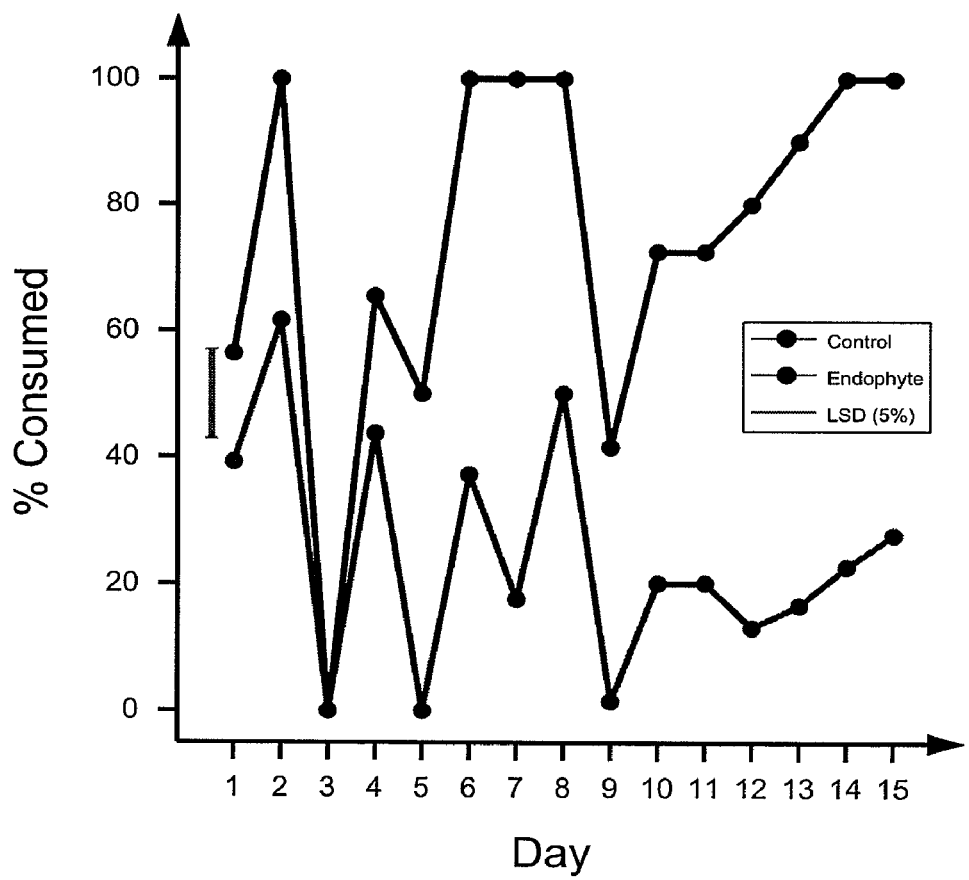
FIG. 18 is a graph that illustrates the percentage of pellets consumed by gulls for different treatments.

As shown in FIG. 18, on days 1 to 3, up to 70% of the endophyte-treated pellets offered were consumed. For the following trial days 4 to 15, of the total amount of pellets consumed, only an average of 30% of the treated pellets per day were consumed. This developed aversion to the endophyte treated pellets shows a learned response or Post Digestion Feed Back (PDF).

Although there was a significant difference between the consumption of treated pellets compared with the untreated control at the onset, this difference rapidly grew larger up to day 15 when the trial was stopped.

Figure 19:
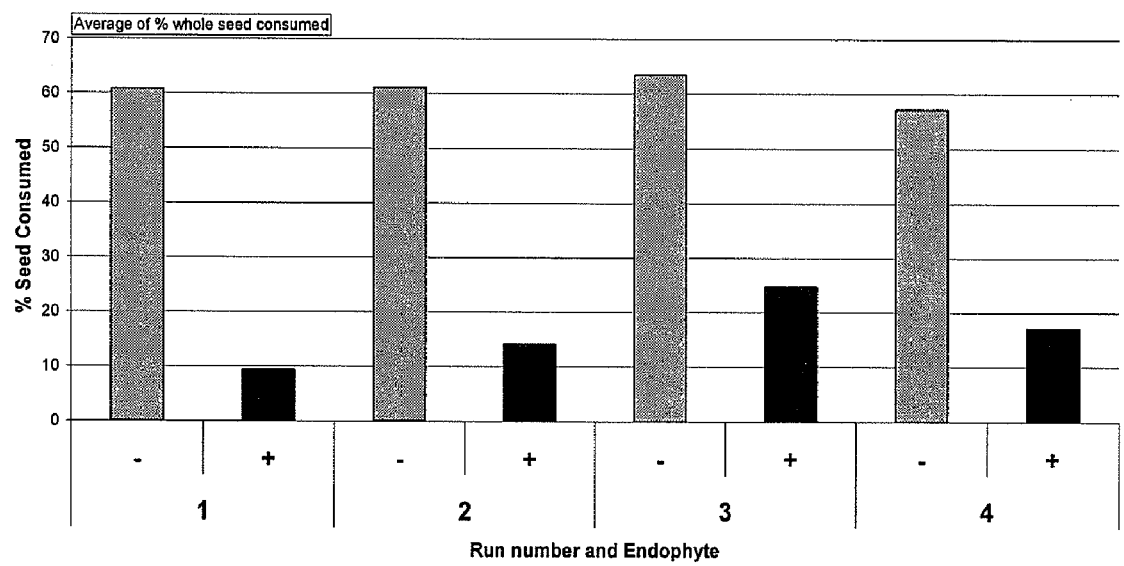
FIG. 19 is a bar chart that illustrates the level of nil endophyte feed eaten by finches compared to endophyte containing feed.

Even though total rejection of the control pellets was not achieved, over time, the divergence of the slopes in FIG. 19 between the treatments is positive. The results with the gulls show promising results for the development of a pellet that can deliver selected endophyte compounds and induce PDF in birds, so that they will subsequently associate normal untreated pig pellets as a source of their malaise. This learned behaviour is dependent on treated pellets looking, smelling and tasting exactly the same as the untreated pellets. The pellets manufactured in this experiment were visually different, and this can contribute to the birds' ability to differentiate between the treated and control pellets, as illustrated at the onset of the trial.

4. Target Avian Species: Finches (*Carduelis choris*)

The inventors in this trial assessed the PDF response of Finches and whether learned behaviour can be shown with a choice between nil-endophyte seed and endophyte containing seed, as described in the next example.

EXAMPLE 10

Capturing and Conditioning the Birds

A number of green finches that were attracted to a granary outside Christchurch were humanely trapped and contained in a facility built for this purpose. The birds were conditioned for six weeks to their new environment and fed bird seed and water on demand.

In the seventh week, nil endophyte ryegrass seed was introduced into the bird seed mix at increasing percentages to condition the birds to this food source. This was conducted for a further six week period, and consumption of the nil endophyte ryegrass was recorded to ascertain how much of this grass seed the birds normally eat.

After the above time period, the birds were fed only water for a period of four hours. Four randomly chosen birds were then captured and separated into individual enclosures. Each bird was then fed on endophyte containing ryegrass seed and later on nil endophyte ryegrass seed.

Results

Figure 20:
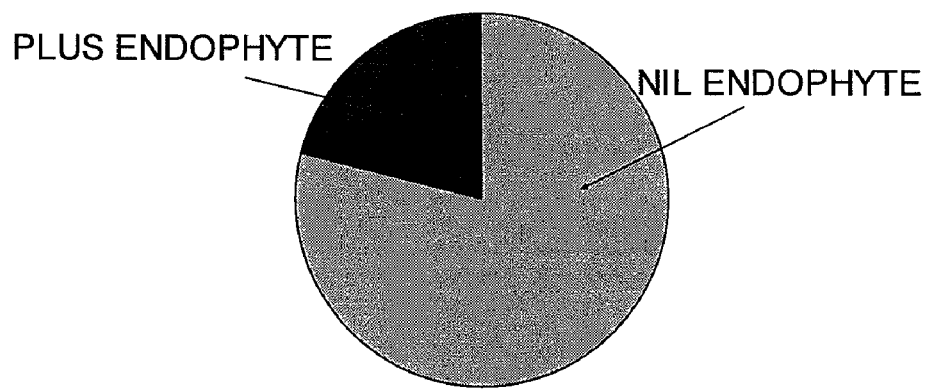
FIG. 20 is a graph showing the average amount of seed consumed for finches between nil endophyte feed consumed versus endophyte containing feed consumed.
Figure 21:
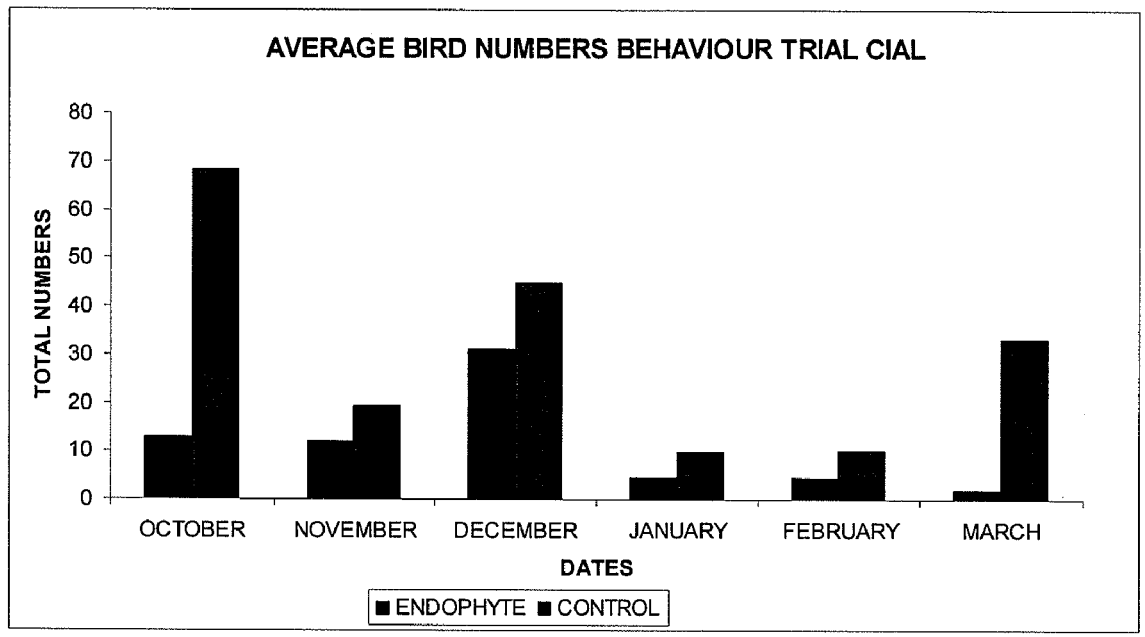
FIG. 21 is a graph showing the total bird numbers present in the endophyte-enhanced plots with the control plots per month for the Christchurch International Airport (CIAL) trial.

The results of the birds' eating behaviour of the nil endophyte seed and endophyte seed is shown in FIGS. 20 and 21. These Figures show a marked decrease in consumption of feed that contained endophyte (10 to 20% of the normal feed consumed for endophyte seed versus 60 to 65% of the normal feed consumed for nil endophyte seed. The results show a genuine repellency by the finches towards endophyte containing seed. Therefore, these results also illustrate a Post Digestive Feed back response to the endophyte containing seed.

5. Christchurch International Airport Trial: Target Avian Species: Wild Birds, Various Species During the autumn of 2007, a trial assessing PDF response on wild birds present at Christchurch International Airport (CIAL) was conducted, as described in the next example.

EXAMPLE 11

Methodology

A number of plots, as outlined in Table 2 below, containing either existing vegetation (control) or planted "Jackal" Tall Fescue (*Festuca arundinacea*) was set up. Each plot was the square size of 50 m by 50 m.

TABLE 2

| PLOT OUTLINE | | |
|---|---|---|
| CONTROL EXISTING SPECIES REP 1 | CONTROL EXISTING SPECIES REP 1 | CONTROL EXISTING SPECIES REP 2 |
| TALL FESCUE ENDOPHYTE REP 1 | TALL FESCUE ENDOPHYTE REP 2 | CONTROL EXISTING SPECIES REP 2 |

The existing vegetation on the control plots consists of plant species, including Hair grass (*Vulpia* sp) and browntop (*Agrostis tenuis*), with small amounts of Yorkshire fog (*Holcus lanatus*), Bromus species, Cocksfoot (*Dactylis glomerata*), Barley grass (*Hordeum* sp), Couch (*Agropyron* sp) and many broadleaf weeds including Wire weed (*Polygonum* sp), Storksbill (*Erodium* sp), and. It was assumed that this vegetation did not contain endophytes.

In comparison, the Tall fescue contained either AR601 or AR604 endophyte strains from the *Neotyphodium coenophialum* species.

During the trial, each plot was monitored daily, at the morning and evening for two minutes. During this time the bird species and numbers was assessed and recorded.

Results

Figure 22:
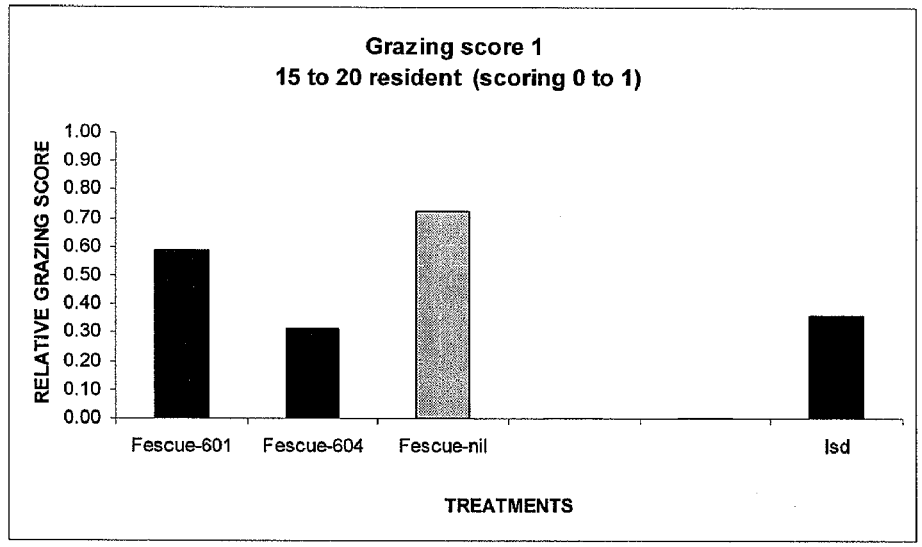
FIG. 22 is a bar chart that illustrates the relative grazing score $1^{st}$ assessment (0=not grazed). LSD 5% shown on right for the Rangiora Sewage treatment plant trial.

The total bird numbers present in the endophyte-enhanced plots with the control plots per month for the trial are shown in FIG. 22. As shown, there was a significant reduction in the number of birds visiting the endophyte plots in comparison to the control plots over the six month period.

The statistical analysis of variance of this trial (shown in Tables 3 to 5 below) showed that even though the data are very variable, the endophyte effects on bird numbers were significant.

TABLE 3

Shows the logarithms of numbers of Birds - 6 month period

| | SS | df | MS | F | P-value |
|---|---|---|---|---|---|
| Endophyte effect | 222.2033 | 1 | 222.2033 | 7.714026 | 0.04995 |
| residual | 115.2204 | 4 | 28.8051 | | |
| Total | 337.4237 | 5 | | | |

Bird numbers were converted to logarithms to smooth variation before statistical analysis

TABLE 4

Shows the means for Endophyte

| Endophyte | 601/604 | Control (existing grasses) |
|---|---|---|
| mean | 11 | 30.83 |
| s.e. | 5.999 | 4.242 |

Two bird counts were made each day. Counts were added for each month.

TABLE 5

Shows the mean accumulated totals per plot for Month

| Date | | | | | |
|---|---|---|---|---|---|
| October | November | December | January | February | March |
| 49.83 | 16.83 | 40.17 | 8 | 8.17 | 22.33 |

Standard error 8.48

6. Rangiora Sewage Treatment Centre: Target Avian Species: Wild Birds, Various Species Following the alkaloid assessment of plants as described under Example 8 above, a field trial to assess the PDF from a variety of bird species was conducted, as described in the next example.

EXAMPLE 12

Method

From the Inoculated Jackal tall fescue plants that were chemo-typed for their alkaloid profile, a number of plants with AR601 and AR604, covering a range of ergovaline (EV) and loline profiles representing three groups, moderate, high and very high EV's. Table 6 below summarises the grass species and ergovaline levels assessed in this trial.

TABLE 6

Selected range of the average ergovaline alkaloid treatments:

| Grass species | average level of ergovaline (ppm) |
| --- | --- |
| Tall Fescue | 15.1 |
| Tall Fescue | 8.7 |
| Tall Fescue | 2.8 |
| Tall Fescue-nil Endo | 0 |

The plants were each divided into four ramets of the same approximate size to get four replicates. All plants were grown over the winter period and rimmed to the same relative size prior to transplanting the plants to the test area—a field at a sewage treatment plant in Rangiora, New Zealand, where wild herbivorous birds are known to frequent. The plants were placed in groups and identified by location using a grid mapping system.

Treatments (nil endophyte and endophyte-infected with 3 levels of ergovaline) were placed in random blocks in the grazing area. Each treatment plant was placed so that the birds had the ability to select in a choice situation.

Assessment

After a grazing period of approximately 5 days depending on bird numbers in the area, each plant was inspected for grazing and assessed on a scale of 0 (no grazing) to 5 (severely grazed). Following scoring, plants were protected from further bird predation to allow sufficient re-growth. The plants were then trimmed off to the same level with a motor mower, watered and fertilised as necessary then fenced to allow for growth recovery. This recovery period was approximately one week depending on the seasonal rainfall.

The area was then re-opened to birds and all plants were inspected every second day and scored when evidence of flock grazing had occurred.

The dominant bird species in October were Canada geese. Later paradise shelducks (in fact another goose species) dominated. Initial assessment cycles were frequent when the local geese, about 20 in number, found the plots. Larger numbers of paradise shelduck (600 to 1500 in the 10 ha pond site) were present from December and due to moulting birds remaining in the area.

For statistical analysis of grazing scores, a mean over all scoring occasions was calculated for each consolidated block of plants of the same group (based on ergovaline measurements).

Results

Feeding Scores

Grazing preference of the birds over the eight observation periods between October 2007 and April 2008.

Figure 23:
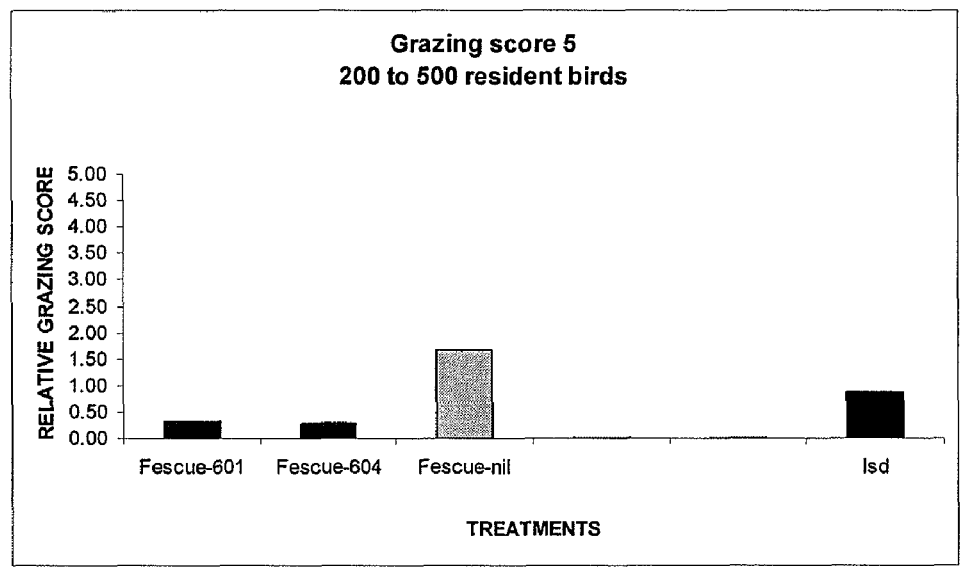
FIG. 23 is a bar chart that illustrates the relative grazing score $5^{th}$ assessment for the Rangiora Sewage treatment plant trial.

At the first sampling period with low bird numbers, most of the endophyte grasses had some repellent properties (See FIG. 23). At the second and third scoring there were no significant differences between any of the treatments. On the next two scorings between the end of October and early December there was a significant result between endophyte plants and nil endophyte (FIG. 24).

For the remaining scorings from mid December to early April all plants were under stress from very large bird numbers. As the birds have to learn that the endophyte grasses can make them ill over time it is our opinion that there were insufficient endophyte plants (or too many geese) in this trial to teach these 600+ birds to avoid grazing.

Figure 24:
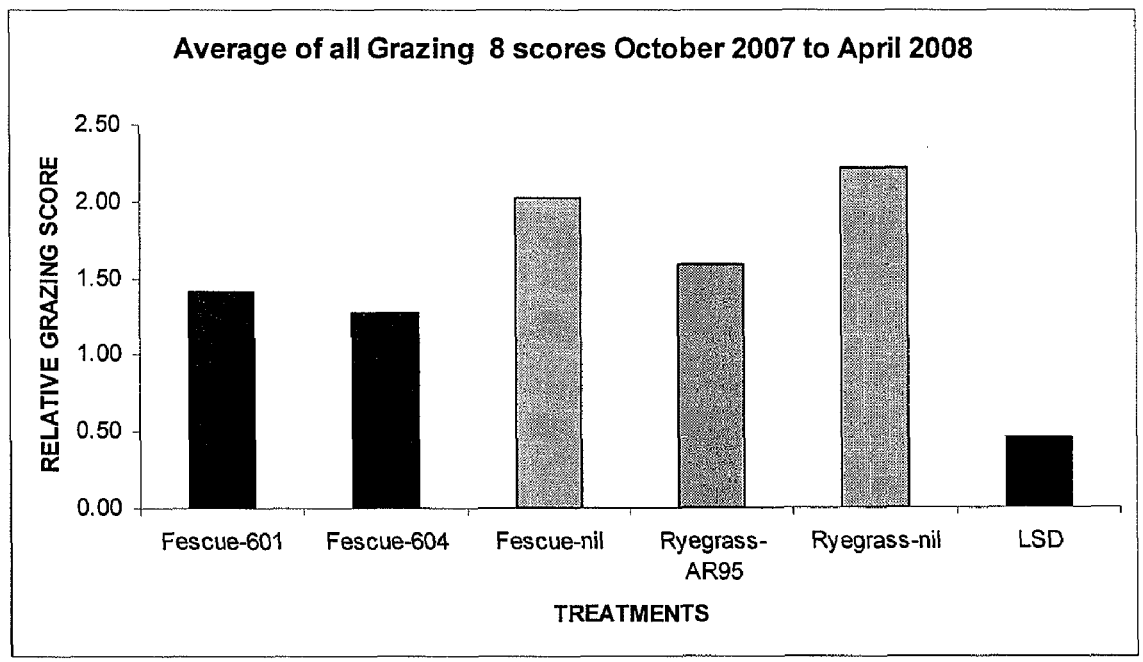
FIG. 24 is a bar chart that illustrates the average grazing scores (mean of 8 grazings) of each endophyte and grass cultivar combination for the Rangiora Sewage treatment plant trial.

Analysis of all scorings for October 2007 to April 2008 looking at the grazing pressure over time has shown that the fescue plants infected with AR601 & AR604 endophyte strains had significant repellence, despite the large bird numbers (Table 7 and 8 and FIG. 24).

TABLE 7

Analysis of variance results of all assessments. Accumulated feeding scores for tall fescue plots

| Source | d.f. | s.s. | m.s. | v.r. | F pr. |
| --- | --- | --- | --- | --- | --- |
| endo | 2 | 2.023 | 1.011 | 14.28 | <.001 |
| rep | 3 | 2.434 | 0.811 | 11.45 | <.001 |
| Residual | 17 | 1.204 | 0.071 | | |
| Total | 22 | 5.661 | 0.257 | | |

TABLE 8

Mean accumulated feeding scores for endophyte treatments for tall fescue plots.

| Endophyte strain | Accumulated feeding score |
| --- | --- |
| AR601 | 1.40 |
| AR604 | 1.18 |
| nil | 2.01 |
| LSD 5%* | 0.34 |

*mean for all comparisons

An additional analysis of the endophyte-infected plots alone showed that the feeding scores on AR604 plots were significantly lower (i.e. less grazed) ($P<0.001$ probability level) than those on AR601 (1.1 v 1.5 respectively).

Survival

At the end of the trial, the number of plants that had survived in this environment under both bird grazing pressure and compacted low fertility stony soils were assessed. The results are shown in Table 9 below.

TABLE 9

Percentage surviving plants in April 2008.

| Cultivar-endophyte | surviving (%) |
| --- | --- |
| Fescue-601 | 53 |
| Fescue-604 | 52 |
| Fescue-nil | 14 |
| LSD 5% | 31 |

The data shows that endophyte infection has enhanced the survival of tall fescue. Drought, severe grazing and perhaps pest pressure have contributed to mortality, but endophyte has influenced the overall outcome.

Minimum Effective Ergovaline Levels:

In analysing the levels of ergovaline necessary to obtain some significant degree of repellence in plants infected with endophyte, there is no difference between levels of material that had previously tested with ergovaline in the range levels between 2.8 and 15 ppm. As shown in Table 10, there is no evidence at this stage that high levels have further reduced grazing scores compared to moderate levels of ergovaline.

TABLE 10

Mean ergovaline levels determined pre-trial (March 2007) and grazing scores for plants.

| Description | Endophyte | Mean ergovaline level (ppm) | Mean grazing score over the season |
|---|---|---|---|
| Jackal tall fescue | AR601 | 2.8† | 1.5* |
| Jackal tall fescue | AR604 | 2.8 | 1.2* |
| Jackal tall fescue | AR601 | 8.7 | 1.5* |
| Jackal tall fescue | AR604 | 8.7 | 1.6 |
| Jackal tall fescue | AR601 | 15.1 | 1.3* |
| Jackal tall fescue | AR604 | 15.1 | 1.1* |
| Jackal tall fescue | NIL | 0 | 2.0 |

LSD 5% = .0.4
*= significantly different from nil endophyte control @ 5%
†ppm = parts per million (mg/kg)

Conclusion

The trial showed that endophyte infection of tall fescue and ryegrass effectively reduces feeding by herbivorous birds and increases plant survival and has shown that increasing the ergovaline concentrations above those in the lower range of the distribution does not affect the result.

7. Endophyte Genotype Analysis

The following example provides microsatellite data to enable a skilled person to identify and confirm whether they are in possession of an endophyte strain or a variation thereof.

EXAMPLE 13

This example enables a person skilled in the art to distinguish endophytes AR601, AR602, AR603, AR604, AR4, AR5, AR8 and AR94 and variations thereof, as described above from other endophytes. In Table 11 below, the endophyte strains and allele sizes at various Simple Sequence Repeats (SSR) are listed, along with the methodology used to arrive at the SSR sizes.

TABLE 11

Summary of Microsatellite data for distinguishing the endophytes referred to in the present application.

| SSR | Allele[1] | Allele size (bp)[2] | AR5 | AR8 | AR94 | AR601 | AR602 | AR603 | AR604 |
|---|---|---|---|---|---|---|---|---|---|
| B10 | b10_01 | 140 | | | | 140 | | | |
| | b10_06 | 162 | | | | | 162 | 162 | 162 |
| | b10_07 | 165 | | | | | | | 165 |
| | b10_09 | 171 | | | | 171 | 171 | 171 | 171 |
| | b10_11 | 176 | 176 | 176 | 176 | | | | |
| | b10_14 | 185 | | | | 185 | 185 | 185 | |
| B11 | b11_16 | 165 | | | | 165 | 165 | 165 | 165 |
| | b11_18 | 177 | | | | | | | |
| | b11_20 | 184 | | | 184 | | | | |
| | b11_22 | 192 | | 192 | | 192 | 192 | 192 | 192 |
| | b11_28 | 237 | 237 | | | | | | |
| ans014 | ans014_02 | 310 | | | | 310 | 310 | 310 | 310 |
| | ans014_05 | 314 | 314 | 314 | 314 | | | | |
| | ans014_07 | 316 | | | | 316 | 316 | 316 | 316 |
| ans016 | ans016_04 | 290 | | | | 290 | 290 | 290 | 290 |
| | ans016_05 | 293 | 293 | 293 | 293 | 293 | 293 | 293 | 293 |
| | ans016_09 | 305 | | | | 305 | 305 | 305 | 305 |
| ans017 | ans017_12 | 300 | | | | 300 | | | |
| | ans017_13 | 305 | | 305 | 305 | | | | |
| | ans017_18 | 315 | | | | | | | 315 |
| | ans017_19 | 318 | | | | | 318 | 318 | |
| | ans017_28 | 362 | 362 | | | | | | |
| | ans017_31 | 388 | | | | | | | |
| ans019 | ans019_01 | 193 | | | | 193 | 193 | 193 | 193 |
| | ans019_03 | 200 | 200 | 200 | 200 | | | | |
| ans025 | ans025_02 | 286 | | | | 286 | 286 | 286 | 286 |
| | ans025_07 | 305 | | 305 | 305 | | | | |
| | ans025_11 | 311 | 311 | | | | | | |
| ans030 | ans030_06 | 325 | 325 | 325 | 325 | | | | |
| | ans030_08 | 331 | | | | 331 | 331 | 331 | 331 |
| ans031 | ans031_10 | 317 | 317 | no data | | 317 | 317 | 317 | 317 |
| | ans031_17 | 341 | | no data | 341 | | | | |
| | ans031_19 | 353 | | no data | | 353 | 353 | 353 | 353 |
| ans036 | ans036_04 | 262 | | | | 262 | 262 | 262 | 262 |
| | ans036_05 | 265 | 265 | 265 | 265 | 265 | 265 | 265 | 265 |

TABLE 11-continued

Summary of Microsatellite data for distinguishing the endophytes referred to in the present application.

| SSR | Allele[1] | Allele size (bp)[2] | AR5 | AR8 | AR94 | AR601 | AR602 | AR603 | AR604 |
|---|---|---|---|---|---|---|---|---|---|
| ans042 | ans042_01 | 123 | | | | 123 | 123 | 123 | 123 |
| | ans042_03 | 130 | | | | 130 | 130 | 130 | 130 |
| | ans042_06 | 140 | | 140 | 140 | | | | |
| | ans042_09 | 150 | | | | | | | |
| | ans042_14 | 184 | 184 | | | | | | |

[1]Allele name is a temporary designation only, based on alleles identified in strain surveys to date
[2]Allele size bin +/−0.5 bp Methodology Used to Locate Simple Sequence Repeats Above in Table 1

DNA Isolation

Genomic DNA was isolated from segments of fresh pseudostem material from endophyte-infected grass using the FastDNA® kit (Q-BIOgene, Irvine, Calif., USA) in conjunction with a FastPrep Cell Disruptor (Q-BIOgene). Genomic DNA is diluted 10× in sterile MilliQ water prior to preparation of polymerase chain reactions (PCR).

Simple Sequence Repeat (SSR) Marker Analysis

The endophyte strains were characterized using primer pairs for SSR markers loci B10, B11, ans014, ans016, ans017, ans019, ans025, ans030, ans031, ans036 and ans042. Primer sequences for these loci are given in Table 12 below. Strain characterizations are conducted using primers synthesized commercially by Integrated DNA Technologies (Coralville, Iowa, USA).

following profile: (1) 94° C. for 4:00 minutes, (2) 30 cycles of: 94° C. for 30 seconds, 60° C. for 30 seconds and 72° C. for 30 seconds, (3) 72° C. for 7 minutes with an iCycler thermocycler (BioRad, Hercules, Calif., USA).

PCR Amplifications Using SSR Markers with the 'ans' Prefix

PCR amplifications use a three-primer system for fluorophore addition (Schuelke 2000). To facilitate this, forward primers are synthesized with a 21 nucleotide M13 tail sequence at the 5'-terminus (sequence 5'-TGTAAAAC-GACGGCCAGT-3' (SEQ ID NO: 23)). The fluorophore used in the PCR reactions is 6-carboxyfluorescein (6-FAM™), but alternative dyes may be used. Reverse primers are synthesized with the sequence 5'-GTTTCTT-3' at the 5'-terminus end, to promote non-templated adenylation at the 3'-terminus end of PCR product (Brownstein et al. 1996). The result of adding the M13 tail sequence and 'pig tail' sequence to the primers is that the expected and observed lengths of PCR

TABLE 12

Primer sequences for simple sequence repeat (SSR) loci used to characterize endophyte strains in planta.

| SSR locus | Forward primer sequence (5'-3') | SEQ ID NO: | Reverse primer sequence (5'-3') | SEQ ID NO: |
|---|---|---|---|---|
| ans014 | CAATCATTCTGAACCAAAACCA | 1 | CCTTATACGCAGGACCAAAGAC | 2 |
| ans016 | CACAAAGACAAACGCCAAAAG | 3 | GCAAAGCTCACAGACAAAGGTC | 4 |
| ans017 | GCCATCCGATAACCTGTCTCTA | 5 | TCGTTTCGGTTCGATTAAGAGT | 6 |
| ans019 | TACCTCTGCACGGTGTATTCC | 7 | TGCATAACACTCACCTTATAGTCG | 8 |
| ans025 | CAGCCCTATTTTATGTTTGAAGG | 9 | GCTCCTGCTTTTATTCCTGCTA | 10 |
| ans030 | GCATAGGAAGTGCTGTTAATTTGA | 11 | AGAGTAGAACCTGCTTGCGTTA | 12 |
| ans031 | ACTCGGAGACATGAAAACCATC | 13 | GACGTGCTCTGTGATGTTGAAT | 14 |
| ans036 | ATTTGCAGCAGAGATGATGTGT | 15 | CCTGCACCGGACTGTTAGTAAT | 16 |
| ans042 | GATGACTACCCGAGTGAGAACC | 17 | AACCCAACAACGTCTTTTCATT | 18 |
| B10 | CGCTCAGGGCTACATACACCATGG | 19 | CTCATCGAGTAACGCAGGCGACG | 20 |
| B11 | CATGGATGGACAAGAGATTGCACG | 21 | TTCACTGCTACAATTCTGTGGAGC | 22 |

PCR amplifications using SSR markers B10 and B11

For both markers B10 and B11 the 5' end of the forward primer is labeled with 6-carboxyfluorescein (6-FAM™) for detection purposes. PCR amplifications were conducted in a 10 μL reaction volume containing 2 μL of diluted genomic DNA, 1.5 mM magnesium chloride, 1×PCR buffer (Invitrogen, Carlsbad, Calif., USA), 0.1 mM of each deoxynucleotide triphosphate (dATP, dGTP, dTTP and dCTP), 0.2 μM each of the forward and reverse primers, and 1 U of Platinum Taq DNA polymerase (Invitrogen). PCR was carried out with the products using the 'ans' SSR primer pairs are increased by 25 basepairs (bp). PCR amplifications are conducted in a 10 μL reaction volume containing 2 μL of diluted genomic DNA, 2.5 mM magnesium chloride, 1×PCR buffer, 0.05 mM of each deoxynucleotide triphosphate (dATP, dGTP, dTTP and dCTP), 0.0375 μM forward primer, 0.15 μM reverse primer, 0.15 μM of fluorescent-labelled M13 primer and 0.5 U of Platinum Taq DNA polymerase. PCR is carried out with the following profile: (1) 94° C. for 4:00 minutes, (2) 30 cycles of: 94° C. for 30 seconds, 55° C. for 30 seconds and 72° C. for 30 seconds, (3) 8 cycles of: 94° C. for 30 seconds, 53° C. for 30 seconds and 72° C. for 30 seconds, (4) 72° C. for 30 minutes (Schuelke 2000) with an iCycler thermocycler.

Genotypic Analysis of SSR Markers

Genotypic analysis was conducted by capillary electrophoresis on an ABI 3100 Genetic Analyser (Applied Biosystems, Foster City, Calif., USA) used POP-7™polymer (Applied Biosystems) and GeneScan™ 500 LIZ™ (Applied Biosystems) as an internal size standard. A run module based on the default Genescan22_POP4DefaultModule is used, with the following changes: run current 200 µA, pre-run voltage 0 kV, pre-run time 1 second, injection voltage 3 kV, injection time 10 seconds, number of steps 1 nk, voltage step interval 1 second, run time 560 seconds. Electropherograms are analysed and PCR fragment size determined using ABI Prism GeneScan (v 3.7, Applied Biosystems). The Genotype data was scored using ABI Prism Genotyper (v 3.7, Applied Biosystems).

CONCLUSIONS

It can therefore be concluded from the above results that:

Selected endophyte infected grasses exhibit a repellent effect on birds.

This repellent effect is a secondary repellent or PDF effect.

Birds are repelled from seeds or herbage of the endophyte and grass cultivar combination.

Ryegrass or tall fescue grasses show the repellent effect depending on the endophyte chosen.

Ergovaline alkaloid is an important toxin that produces the avian repellent effect.

Peramine and loline alkaloids are also useful to confer resistance to biotic and abiotic stresses on the grass.

A combination of AR4, AR5, AR8 or AR94 endophyte with a ryegrass cultivar are good candidates for avian repellent applications, owing to their repellent levels of the alkaloid ergovaline and insect resistance conferred by peramine and/or loline alkaloids.

A tall fescue and AR601 or AR604 endophyte combination can be used as avian repellent and additionally provide good insect resistance.

Other suitable candidates include, AR602 or AR603 with tall fescue as these combinations also display higher levels of ergovaline and peramine and/or lolitrem alkaloids.

Embodiments of the present invention have been described by way of example only, and it is appreciated that modifications and additions can be made thereto without departing from the scope thereof as defined in the appended claims.

What we claim is:

1. An endophyte and grass cultivar combination that repels avian species from the combination, said combination comprising an isolated endophyte in combination with a grass cultivar, wherein the endophyte is selected from the group consisting of: AR601, AR602, AR603, AR604, (Deposit Nos. V07/029058, V07/029059, V07/029060, V07/029061).

2. The combination as claimed in claim 1, wherein the combination produces ergovaline alkaloid compound at a level of at least 2.8 ppm within a portion of the cultivar herbage and seeds produced therefrom sufficient to repel the avian species from the cultivar herbage and seeds produced therefrom.

3. The combination as claimed in claim 1 wherein the endophyte and grass cultivar combination repel avian species via a secondary deterrent effect.

4. The combination as claimed in claim 1 wherein the endophyte and grass cultivar combination repel avian species via a post digestive feedback (PDF) mechanism.

5. The combination as claimed in claim 1 wherein the ergovaline is present in a range from 2.8 ppm to 100 ppm.

6. The combination as claimed in claim 1 wherein the combination comprises a synthetic grass cultivar.

7. The combination as claimed in claim 1 wherein the avian species is selected from the group consisting of: geese species, seagull species, sparrow species, finch species, lapwing species, and combinations thereof.

8. The combination as claimed in claim 1 wherein the endophyte is also characterised in that it confers resistance to the combination against biotic and abiotic stresses.

9. The combination as claimed in claim 8 wherein the biotic stress is resistance to attack from insects and pests.

10. The combination as claimed in claim 8 wherein the abiotic stresses are selected from the group consisting of: resistance to drought or dry periods, and resistance to high or low temperature climates.

11. The combination as claimed in claim 8 wherein the endophyte is also characterised in that it produces loline alkaloids within at least a portion of the cultivar herbage and seeds produced therefrom.

12. The combination as claimed in claim 11 wherein the loline is present in a range from 1 ppm to 9500 ppm.

13. The combination as claimed in claim 1 wherein the endophyte is also characterised in that it produces peramine alkaloids compounds within at least a portion of the cultivar herbage and seeds produced therefrom.

14. The combination as claimed in claim 13 wherein the peramine is present in a range from 1 ppm to 100 ppm.

15. An endophyte and *Festuca* grass cultivar combination including an isolated endophyte selected from the group consisting of: AR601, AR602, AR603, and AR604, (Deposit Nos. V07/029,058, V07/029,059, V07/029,060, V07/029,061) and combinations thereof;
wherein avian species are repelled from the cultivar herbage and seeds produced therefrom.

16. The combination as claimed in claim 15, wherein the endophyte in the combination produces a level of at least 2.8 ppm of ergovaline alkaloid compound within a portion of the cultivar herbage and seeds produced therefrom.

17. The combination as claimed in claim 15 wherein the grass cultivar is tall fescue.

18. A method of repelling avian species from an area of land by planting an endophyte and grass cultivar as claimed in claim 1 on or adjacent the land from which the avian species are to be repelled from.

19. An isolated endophyte selected from the group consisting of: AR601, AR602, AR603, AR604, (Deposit Nos. V07/029058, V07/029059, V07/029060, and V07/029061), and combinations thereof.

20. The combination as claimed in claim 15, wherein the loline alkaloid concentration within a portion of the cultivar herbage and seeds produced therefrom is at least 1000 ppm.

21. The isolated endophyte as claimed in claim 19, wherein said endophyte is AR601 (Deposit No. V07/029058).

22. The isolated endophyte as claimed in claim 19, wherein said endophyte is AR602 (Deposit No. V07/029059).

23. The isolated endophyte as claimed in claim 19, wherein said endophyte is AR603 (Deposit No. V07/029060).

24. The isolated endophyte as claimed in claim 19, wherein said endophyte is AR604 (Deposit No. V07/029061).

* * * * *

UNITED STATES PATENT AND TRADEMARK OFFICE
CERTIFICATE OF CORRECTION

| | | |
|---|---|---|
| PATENT NO. | : 8,101,400 B2 | |
| APPLICATION NO. | : 12/110159 | |
| DATED | : January 24, 2012 | |
| INVENTOR(S) | : Maurice Philip Rolston et al. | |

It is certified that error appears in the above-identified patent and that said Letters Patent is hereby corrected as shown below:

Title Page, (Item 56), Column 2, Line 25, Under Other Publications, change "impOlications" to --implications--.

Title Page, (Item 57), Abstract, Line 10, Change "V071029056," to --V07/029056,--.

On Sheet 4 of 12 (X-Axis) (Figure 7), Line 2, Change "Endosfe" to --Endosafe--.

On Sheet 4 of 12 (X-Axis) (Figure 8), Line 2, Change "Endosfe" to --Endosafe--.

In Column 2, Line 23, Change "reproducable" to --reproducible--.

In Column 7, Line 48, Change "lolitrem" to --loline--.

In Column 8, Line 33 (Approx.), Change "Grazig" to --Grazing--.

In Column 8, Line 38 (Approx.), Change "animals'long" to --animals' long--.

In Column 8, Line 55, Change "praire" to --prairie--.

In Column 8, Line 63, Change "Grazig" to --Grazing--.

In Column 11, Line 36, Change "martial" to --material--.

In Column 13, Line 63, Change "lolitrem" to --loline--.

In Column 13, Line 66, Change "lolitrem" to --loline--.

In Column 15, Line 1, Change "tall fescue" to --ryegrass--.

Signed and Sealed this
Twelfth Day of February, 2013

Teresa Stanek Rea
*Acting Director of the United States Patent and Trademark Office*

CERTIFICATE OF CORRECTION (continued)
U.S. Pat. No. 8,101,400 B2

In Column 15, Line 2, Change "tall fescue" to --ryegrass--.

In Column 15, Line 16, Change "combinations" to --combinations.--.

In Column 15, Line 18, Change "lolitrem" to --loline--.

In Column 15, Line 45, Change "endophytes" to --endophytes.--.

In Column 15, Line 52 (Approx.), Change "where" to --were--.

In Column 17, Line 22, Change "choris" to --chloris--.

In Column 18, Line 17, Change "and. It" to --and it--.

In Column 21, Line 23 (Approx.), Change ".0.4" to --0.4--.

In Column 26, Line 13, Change "loline" to --lolitrem--.

In Column 26, Line 19, Change "lolitrem" to --loline--.

In Column 34, Line 12-13 (Approx.), In Claim 15, change "V07/029,058, V07/029,059, V07/029,060, V07/029,061)" to --V07/029058, V07/029059, V07/029060, V07/029061)--.

SEQUENCE LISTING

```
<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 1
caatcattct gaaccaaaac ca                                              22

<210> SEQ ID NO 2
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 2
ccttatacgc aggaccaaag ac                                              22

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 3
cacaaagaca aacgccaaaa g                                               21

<210> SEQ ID NO 4
<211> LENGTH: 22
<212> TYPE: DNA
<213> ORGANISM: Artificial Sequence
<220> FEATURE:
<223> OTHER INFORMATION: Oligonucleotide Primer
```

```
<400> SEQUENCE: 4
gcaaagctca cagacaaagg tc                                              22

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 5
gccatccgat aacctgtctc ta                                              22

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 6
tcgtttcggt tcgattaaga gt                                              22

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 7
tacctctgca cggtgtattc c                                               21

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 8
tgcataacac tcaccttata gtcg                                            24

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 9
cagccctatt ttatgtttga agg                                             23

<210> SEQ ID NO 10
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 10
gctcctgctt ttattcctgc ta                                              22
```

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 11
gcataggaag tgctgttaat ttga                                    24

<210> SEQ ID NO 12
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 12
agagtagaac ctgcttgcgt ta                                      22

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 13
actcggagac atgaaaacca tc                                      22

<210> SEQ ID NO 14
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 14
gacgtgctct gtgatgttga at                                      22

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 15
atttgcagca gagatgatgt gt                                      22

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 16
cctgcaccgg actgttagta at                                      22

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide Primer

```
<400> SEQUENCE: 17
gatgactacc cgagtgagaa cc                                            22

<210> SEQ ID NO 18
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 18
aacccaacaa cgtcttttca tt                                            22

<210> SEQ ID NO 19
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 19
cgctcagggc tacatacacc atgg                                          24

<210> SEQ ID NO 20
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 20
ctcatcgagt aacgcaggcg acg                                           23

<210> SEQ ID NO 21
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 21
catggatgga caagagattg cacg                                          24

<210> SEQ ID NO 22
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 22
ttcactgcta caattctgtg gagc                                          24

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 23
tgtaaaacga cggccagt                                                 18
```